United States Patent
Yamaguchi et al.

(10) Patent No.: US 7,161,032 B2
(45) Date of Patent: Jan. 9, 2007

(54) SULFONAMIDE DERIVATIVES, INSECTICIDES FOR AGRICULTURAL AND HORTICULTURAL USE, AND USAGE THEREOF

(75) Inventors: Minoru Yamaguchi, Kawachinagano (JP); Hayami Nakao, Kawachinagano (JP); Makoto Goto, Kawachinagano (JP); Masayuki Morimoto, Kawachinagano (JP); Shinsuke Fujioka, Kawachinagano (JP); Masanori Tohnishi, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 88 days.

(21) Appl. No.: 10/525,504

(22) PCT Filed: Aug. 26, 2003

(86) PCT No.: PCT/JP03/10774

§ 371 (c)(1),
(2), (4) Date: Feb. 23, 2005

(87) PCT Pub. No.: WO2004/018415

PCT Pub. Date: Mar. 4, 2004

(65) Prior Publication Data

US 2006/0167315 A1    Jul. 27, 2006

(30) Foreign Application Priority Data

Aug. 26, 2002 (JP) ............................. 2002-245264

(51) Int. Cl.
*C07C 303/00* (2006.01)
*A01N 25/26* (2006.01)
*A01N 25/34* (2006.01)
*C05G 3/00* (2006.01)

(52) U.S. Cl. ........................... 564/84; 564/86; 564/91; 504/100; 504/101; 424/405; 424/416

(58) Field of Classification Search ...................... None
See application file for complete search history.

(56) References Cited

FOREIGN PATENT DOCUMENTS

| WO | WO 01/46124 | 6/2001 |
| WO | WO 02/94766 | 11/2002 |
| WO | WO 03/11028 | 2/2003 |

*Primary Examiner*—Sikarl A. Witherspoon
(74) *Attorney, Agent, or Firm*—Paul E. White, Jr.; Manelli Denison & Selter PLLC

(57) ABSTRACT

Sulfonamide derivatives represented by general formula (I) or salts thereof; insecticides for agricultural and horticultural use containing the same as the active ingredient; and usage thereof:

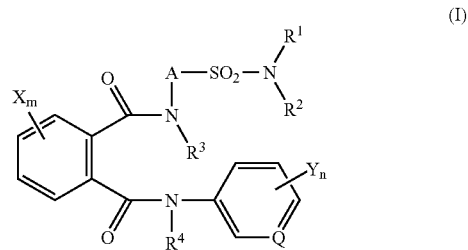

(I)

[wherein A is optionally substituted $(C_1$–$C_6)$alkylene, $(C_3$–$C_6)$alkenylene or the like; $R^1$ is H, optionally substituted $(C_1$–$C_6)$alkyl, $(C_3$–$C_6)$alkenyl, $(C_3$–$C_6)$cycloalkyl or the like; $R^2$, $R^3$ and $R^4$ are each H, $(C_1$–$C_6)$alkyl, $(C_3$–$C_6)$ alkenyl or the like, or $R^2$ and A or $R^2$ and $R^1$ may form a 3- to 8-membered ring which may be interrupted by one to three atoms selected from among O, S and N; Q is C or N; X and Y are each halogen, CN, $NO_2$, $(C_1$–$C_6)$alkyl, $(C_2$–$C_6)$ alkenyl or the like; m is 0 to 2; n is 0 to 3; and two adjacent Xs or Ys on the aromatic ring may be united to form a fused ring]. The compounds exhibit excellent insecticidal activity against insect pests resistant to existing pesticides even when applied in dosages lower than those of similar pesticides.

3 Claims, No Drawings

SULFONAMIDE DERIVATIVES, INSECTICIDES FOR AGRICULTURAL AND HORTICULTURAL USE, AND USAGE THEREOF

This application is the national phase of international application PCT/JP03/10774 filed 26 Aug. 2003 which designated the U.S.

TECHNICAL FIELD

The present invention relates to sulfonamide derivatives or salts thereof, agricultural and horticultural insecticides containing any of said compounds as an active ingredient, and their usage.

BACKGROUND ART

Compounds analogous to the sulfonamide derivatives of the present invention have been known to be useful as agricultural and horticultural insecticides (see, for example, JP-A-11-240857 or JP-A-2001-131141). These references, however, do not describe working examples, physical properties and the like with respect to the compounds represented by general formula (I) of the present invention.

The production of agricultural and horticultural crops and the like is still badly damaged by insect pests and the like, and the development of a novel agricultural and horticultural insecticide is desired because of, for example, the appearance of insect pests resistant to existing chemicals. In addition, because of the increased population of aged farmers, and the like, various labor-saving application methods are desired and the development of an agricultural and horticultural insecticide having properties suitable for the application methods is desired.

DISCLOSURE OF THE INVENTION

The present inventors earnestly investigated in order to develop a novel agricultural and horticultural insecticide, and consequently found that the sulfonamide derivatives represented by general formula (I) or salts thereof of the present invention are novel compounds not known in any literature and are excellent agricultural and horticultural insecticides which are effective at a lower dosage as compared with the analogous compounds disclosed in the above prior art references, whereby the present invention has been accomplished.

That is, the present invention relates to sulfonamide derivatives represented by general formula (I), or salts thereof:

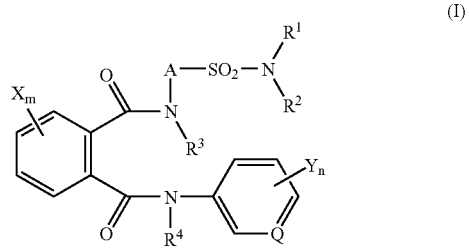

(I)

wherein A is a $(C_1-C_6)$alkylene group; a substituted $(C_1-C_6)$ alkylene group having one or more substituents which may be the same or different and are selected from halogen atoms, cyano group, nitro group, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups and di$(C_1-C_6)$alkylamino groups whose $(C_1-C_6)$ alkyl groups may be the same or different; a $(C_3-C_6)$ alkenylene group; a substituted $(C_3-C_6)$alkenylene group having one or more substituents which may be the same or different and are selected from halogen atoms, cyano group, nitro group, $(C_1-C_6)$alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups and di$(C_1-C_6)$alkylamino groups whose $(C_1-C_6)$alkyl groups may be the same or different; a $(C_3-C_6)$alkynylene group; or a substituted $(C_3-C_6)$alkynylene group having one or more substituents which may be the same or different and are selected from halogen atoms, cyano group, nitro group, $(C_1-C_6)$alkoxy groups, halo$(C_1-C_6)$alkoxy groups, $(C_1-C_6)$ alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups and di$(C_1-C_6)$ alkylamino groups whose $(C_1-C_6)$alkyl groups may be the same or different; any saturated carbon atom in the $(C_1-C_6)$ alkylene group, substituted $(C_1-C_6)$alkylene group, $(C_3-C_6)$ alkenylene group, substituted $(C_3-C_6)$alkenylene group, $(C_3-C_6)$alkynylene group or substituted $(C_3-C_6)$alkynylene group may be substituted by a $(C_2-C_5)$alkylene group so as to form a $(C_3-C_6)$cycloalkane ring, and any two carbon atoms in the $(C_2-C_6)$alkylene group, substituted $(C_2-C_6)$ alkylene group, $(C_3-C_6)$alkenylene group or substituted $(C_3-C_6)$alkenylene group may be taken together with an alkylene group or an alkenylene group so as to represent a $(C_3-C_6)$cycloalkane ring or a $(C_3-C_6)$cycloalkene ring;

$R^1$ is a hydrogen atom; a $(C_1-C_6)$alkyl group; a substituted $(C_1-C_6)$alkyl group having one or more substituents which may be the same or different and are selected from halogen atoms, cyano group, nitro group, hydroxyl group, $(C_1-C_6)$alkoxy groups, halo$(C_1-C_6)$alkoxy groups, $(C_1-C_6)$ alkylthio groups, halo$(C_1-C_6)$alkylthio groups, $(C_1-C_6)$ alkylsulfinyl groups, halo$(C_1-C_6)$alkylsulfinyl groups, $(C_1-C_6)$alkylsulfonyl groups, halo$(C_1-C_6)$alkylsulfonyl groups, mono$(C_1-C_6)$alkylamino groups, mono(halo$(C_1-C_6)$alkyl)amino groups, di$(C_1-C_6)$alkylamino groups whose $(C_1-C_6)$alkyl groups may be the same or different, di(halo$(C_1-C_6)$alkyl)amino groups whose halo$(C_1-C_6)$alkyl groups may be the same or different, $(C_1-C_6)$alkoxycarbonyl groups, $(C_1-C_6)$alkylaminocarbonyl groups, $(C_1-C_6)$ alkylcarbonyloxy groups, phenoxy group, substituted phenoxy groups having one or more substituents which may be the same or different and are selected from halogen atoms, $(C_1-C_6)$alkyl groups, halo$(C_1-C_6)$alkyl groups, $(C_1-C_6)$ alkoxy groups, halo$(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$ alkylsulfonyl groups, halo$(C_1-C_6)$alkylsulfonyl groups and $(C_1-C_6)$alkoxycarbonyl groups, phenylthio group, substituted phenylthio groups having one or more substituents which may be the same or different and are selected from halogen atoms, $(C_1-C_6)$alkyl groups, halo $(C_1-C_6)$alkyl groups, $(C_1-C_6)$alkoxy groups, halo $(C_1-C_6)$alkoxy groups, $(C_1-C_6)$alkylthio groups, halo$(C_1-C_6)$alkylthio groups, $(C_1-C_6)$alkylsulfinyl groups, halo$(C_1-C_6)$alkylsulfinyl groups, $(C_1-C_6)$alkylsulfonyl groups, halo$(C_1-C_6)$alkylsulfonyl groups and $(C_1-C_6)$alkoxycarbonyl groups, phenyl group, substituted phenyl groups having one or more substituents which may be the same or different and are selected from halogen atoms, cyano group, nitro group, $(C_1-C_6)$alkyl groups, halo($C_1$–$C_6$)alkyl groups, ($C_1$–$C_6$)alkoxy groups, halo($C_1$–$C_6$)alkoxy groups, mono($C_1$–$C_6$)alkylamino groups, di($C_1$–$C_6$)alkylamino groups whose ($C_1$–$C_6$)alkyl groups may be the same or different, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups and ($C_1$–$C_6$)alkoxycarbonyl groups, pyridyl group, and substituted pyridyl groups having one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, mono($C_1$–$C_6$)alkylamino groups, di($C_1$–$C_6$)alkylamino groups whose ($C_1$–$C_6$)alkyl groups may be the same or different, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups and ($C_1$–$C_6$)alkoxycarbonyl groups; a ($C_3$–$C_6$)alkenyl group; a halo($C_3$–$C_6$)alkenyl group; a ($C_3$–$C_6$)alkynyl group; a halo($C_3$–$C_6$)alkynyl group; a ($C_3$–$C_6$)cycloalkyl group; a hydroxyl group; a ($C_1$–$C_6$)alkoxy group; a halo($C_1$–$C_6$)alkoxy group; an amino group; a mono($C_1$–$C_6$)alkylamino group; a mono(halo($C_1$–$C_6$)alkyl)amino group; a di($C_1$–$C_6$)alkylamino group whose ($C_1$–$C_6$)alkyl groups may be the same or different; a di(halo($C_1$–$C_6$)alkyl)amino group whose halo($C_1$–$C_6$)alkyl groups may be the same or different; a ($C_1$–$C_6$)alkylcarbonylamino group; a phenylamino group; a substituted phenylamino group having on the ring one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)alkylamino groups, mono(halo($C_1$–$C_6$)alkyl)amino groups, di($C_1$–$C_6$)alkylamino groups whose ($C_1$–$C_6$)alkyl groups may be the same or different, di(halo($C_1$–$C_6$)alkyl)amino groups whose halo($C_1$–$C_6$)alkyl groups may be the same or different, ($C_1$–$C_6$)alkoxycarbonyl groups and ($C_1$–$C_6$)alkylaminocarbonyl groups; a benzoylamino group; a substituted benzoylamino group having on the ring one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)alkylamino groups, mono(halo($C_1$–$C_6$)alkyl)amino groups, di($C_1$–$C_6$)alkylamino groups whose ($C_1$–$C_6$)alkyl groups may be the same or different, di(halo($C_1$–$C_6$)alkyl)amino groups whose halo($C_1$–$C_6$)alkyl groups may be the same or different, ($C_1$–$C_6$)alkoxycarbonyl groups and ($C_1$–$C_6$)alkylaminocarbonyl groups; —N=C($T^1$)$T^2$ (wherein each of $T^1$ and $T^2$, which may be the same or different, is a hydrogen atom, a ($C_1$–$C_6$)alkyl group, a halo($C_1$–$C_6$)alkyl group, a phenyl group or a substituted phenyl group having one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)alkylamino groups, mono(halo($C_1$–$C_6$)alkyl)amino groups, di($C_1$–$C_6$)alkylamino groups whose ($C_1$–$C_6$)alkyl groups may be the same or different, di(halo($C_1$–$C_6$)alkyl)amino groups whose halo($C_1$–$C_6$)alkyl groups may be the same or different, ($C_1$–$C_6$)alkoxycarbonyl groups and ($C_1$–$C_6$)alkylaminocarbonyl groups); a phenyl group; a substituted phenyl group having one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)alkylamino groups, mono(halo($C_1$–$C_6$)alkyl)amino groups, di($C_1$–$C_6$)alkylamino groups whose ($C_1$–$C_6$)alkyl groups may be the same or different, di(halo($C_1$–$C_6$)alkyl)amino groups whose halo($C_1$–$C_6$)alkyl groups may be the same or different, and ($C_1$–$C_6$)alkoxycarbonyl groups; a pyridyl group; or a substituted pyridyl group having one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)alkylamino groups, mono(halo($C_1$–$C_6$)alkyl)amino groups, di($C_1$–$C_6$)alkylamino groups whose ($C_1$–$C_6$)alkyl groups may be the same or different, di(halo($C_1$–$C_6$)alkyl)amino groups whose halo($C_1$–$C_6$)alkyl groups may be the same or different, and ($C_1$–$C_6$)alkoxycarbonyl groups;

each of $R^2$, $R^3$ and $R^4$, which may be the same or different, is a hydrogen atom, a ($C_1$–$C_6$)alkyl group, a ($C_3$–$C_6$)alkenyl group, a ($C_3$–$C_6$)alkynyl group, a ($C_1$–$C_4$)alkoxy($C_1$–$C_4$)alkyl group or a ($C_1$–$C_4$)alkylthio($C_1$–$C_4$)alkyl group, $R^2$ being able to bind to A or $R^1$ to form a 3- to 8-membered ring which may contain one to three atoms that may be the same or different and are selected from oxygen atom, sulfur atom and nitrogen atom, and which ring may have one or more substituents that may be the same or different and are selected from halogen atoms, ($C_1$–$C_6$)alkyl groups and ($C_1$–$C_6$)alkoxy groups, and $R^2$ being able to be taken together with $R^1$ to represent =C($T^3$)$T^4$ (wherein each of $T^3$ and $T^4$, which may be the same or different, is a hydrogen atom, a ($C_1$–$C_6$)alkyl group, a halo($C_1$–$C_6$)alkyl group, a ($C_1$–$C_6$)alkoxy group, a halo($C_1$–$C_6$)alkoxy group, an amino group, a mono($C_1$–$C_6$)alkylamino group, a di($C_1$–$C_6$)alkylamino group whose ($C_1$–$C_6$)alkyl groups may be the same or different, a mono(halo($C_1$–$C_6$)alkyl)amino group, a di(halo($C_1$–$C_6$)alkyl)amino group whose halo($C_1$–$C_6$)alkyl groups may be the same or different, a phenyl group or a substituted phenyl group having one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)alkylamino groups, mono(halo($C_1$–$C_6$)alkyl)amino groups, di($C_1$–$C_6$)alkylamino groups whose ($C_1$–$C_6$)alkyl groups may be the same or different, di(halo($C_1$–$C_6$)alkyl)amino groups whose halo($C_1$–$C_6$)alkyl groups may be the same or different, ($C_1$–$C_6$)alkoxycarbonyl groups and ($C_1$–$C_6$)alkylaminocarbonyl groups);

Q is a carbon atom or a nitrogen atom;

each of Xs, which may be the same or different, is a halogen atom, a cyano group, a nitro group, an amino group, a ($C_1$–$C_6$)alkyl group, a halo($C_1$–$C_6$)alkyl group, a ($C_2$–$C_6$)alkenyl group, a halo($C_2$–$C_6$)alkenyl group, a ($C_2$–$C_6$)alkynyl group, a halo($C_3$–$C_6$)alkynyl group, a ($C_1$–$C_6$)alkoxy group, a halo($C_1$–$C_6$)alkoxy group, a ($C_1$–$C_6$)alkylcarbonyloxy group, a halo($C_1$–$C_6$)alkylcarbonyloxy group, a ($C_1$–$C_6$)alkylthio group, a halo($C_1$–$C_6$)alkylthio group, a ($C_1$–$C_6$)alkylsulfinyl group, a halo($C_1$–$C_6$)alkylsulfinyl group, a ($C_1$–$C_6$)alkylsulfonyl group, a halo($C_1$–$C_6$)alkylsulfonyl group, a ($C_1$–$C_6$)alkylsulfonyloxy group, a halo($C_1$–$C_6$)alkylsulfonyloxy group, a mono($C_1$–$C_6$)-alkylamino group, a mono(halo($C_1$–$C_6$)alkyl)amino group, a di($C_1$–$C_6$)alkylamino group whose ($C_1$–$C_6$)alkyl groups may be the same or different, a di(halo($C_1$–$C_6$)alkyl)amino group whose halo($C_1$–$C_6$)alkyl groups may be the same or different, a ($C_1$–$C_6$)alkylcarbonylamino group, a halo($C_1$–$C_6$)alkylcarbonylamino group, a ($C_1$–$C_6$)alkylsulfonylamino group or a halo($C_1$–$C_6$)alkylsulfonylamino group, further, two adjacent Xs on the aromatic ring being able to be taken together to represent a fused ring that may have one or more substituents which may be the same or different and are selected from halogen atoms, nitro group, cyano group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)alkylamino groups, mono(halo($C_1$–$C_6$)alkyl)amino groups, di($C_1$–$C_6$)alkylamino groups whose ($C_1$–$C_6$)alkyl groups may be the same or different, and di(halo($C_1$–$C_6$)alkyl)amino groups whose halo($C_1$–$C_6$)alkyl groups may be the same or different, m is an integer of 0 to 2;

each of Ys, which may be the same or different, is a halogen atom; a cyano group; a nitro group; a hydroxyl group; a formyl group; a ($C_1$–$C_6$)alkyl group; a hydroxy ($C_1$–$C_6$)alkyl group; a ($C_1$–$C_6$)alkoxy($C_1$–$C_6$)alkyl group; a halo($C_1$–$C_6$)alkoxy($C_1$–$C_6$)alkyl group; a halo($C_1$–$C_6$)alkyl group; a hydroxyhalo($C_1$–$C_6$)alkyl group; a ($C_1$–$C_6$)alkoxyhalo($C_1$–$C_6$)alkyl group; a halo($C_1$–$C_6$)alkoxyhalo($C_1$–$C_6$) alkyl group; a ($C_1$–$C_6$)alkoxy group; a halo($C_1$–$C_6$)alkoxy group; a halo($C_1$–$C_6$)alkoxyhalo($C_1$–$C_6$)alkoxy group; a ($C_1$–$C_6$)alkylthio group; a halo($C_1$–$C_6$)alkylthio group; a ($C_1$–$C_6$)alkylsulfinyl group; a halo($C_1$–$C_6$)alkylsulfinyl group; a ($C_1$–$C_6$)alkylsulfonyl group; a halo($C_1$–$C_6$)alkylsulfonyl group; a halo($C_1$–$C_6$)alkoxyhalo($C_1$–$C_6$)alkylthio group; a halo($C_1$–$C_6$)alkoxyhalo($C_1$–$C_6$)alkylsulfinyl group; a halo($C_1$–$C_6$)alkoxyhalo($C_1$–$C_6$)alkylsulfonyl group; a phenoxy group; a substituted phenoxy group having one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$)alkylsulfonyl groups; a phenylthio group; a substituted phenylthio group having one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$)alkylsulfonyl groups; a pyridyloxy group; or a substituted pyridyloxy group having one or more substituents which may be the same or different and are selected from halogen atoms, cyano group, nitro group, ($C_1$–$C_6$)alkyl groups, halo($C_1$–$C_6$)alkyl groups, ($C_1$–$C_6$)alkoxy groups, halo($C_1$–$C_6$)alkoxy groups, ($C_1$–$C_6$)alkylthio groups, halo($C_1$–$C_6$)alkylthio groups, ($C_1$–$C_6$)alkylsulfinyl groups, halo($C_1$–$C_6$)alkylsulfinyl groups, ($C_1$–$C_6$)alkylsulfonyl groups and halo($C_1$–$C_6$)alkylsulfonyl groups, further, two adjacent Ys on the aromatic ring being able to be taken together to represent a fused ring that may have one or more substituents which may be the same or different and are selected from halogen atoms, nitro group, cyano group, ($C_1$–$C_6$)alkyl groups, halo ($C_1$–$C_6$)alkyl groups, ($C_1$–$C_6$)alkoxy groups, halo ($C_1$–$C_6$)alkoxy groups, ($C_1$–$C_6$) alkylthio groups, halo($C_1$–$C_6$)alkylthio groups, ($C_1$–$C_6$) alkylsulfinyl groups, halo($C_1$–$C_6$)alkylsulfinyl groups, ($C_1$–$C_6$)alkylsulfonyl groups, halo($C_1$–$C_6$)alkylsulfonyl groups, mono($C_1$–$C_6$)alkylamino groups, mono(halo ($C_1$–$C_6$)alkyl)amino groups, di($C_1$–$C_6$)alkylamino groups whose ($C_1$–$C_6$)alkyl groups may be the same or different, and di(halo($C_1$–$C_6$)alkyl)amino groups whose halo($C_1$–$C_6$) alkyl groups may be the same or different, and n is an integer of 0 to 3; an agricultural and horticultural insecticide containing said compound as an active ingredient, and a method of using the same.

MODE FOR CARRYING OUT THE INVENTION

In the definition of general formula (I) for the sulfonamide derivative of the present invention, the term "halogen atom" means a chlorine atom, a bromine atom, an iodine atom or a fluorine atom. The term "($C_1$–$C_6$)alkyl" means a linear or branched alkyl group of 1 to 6 carbon atoms, such as methyl, ethyl, n-propyl, i-propyl, n-butyl, i-butyl, s-butyl, t-butyl, n-pentyl, n-hexyl or the like. The term "halo($C_1$–$C_6$)alkyl" means a substituted linear or branched alkyl group of 1 to 6 carbon atoms having as the substituent(s) one or more halogen atoms which may be the same or different. The term "($C_3$–$C_6$)cycloalkyl" means a cyclic alkyl group of 3 to 6 carbon atoms, such as cyclopropyl, cyclobutyl, cyclopentyl, cyclohexyl or the like. The term "($C_1$–$C_6$)alkylene" means a linear or branched alkylene group of 1 to 6 carbon atoms, such as methylene, ethylene, propylene, trimethylene, dimethylmethylene, tetramethylene, isobutylene, dimethylethylene or the like. The term "($C_2$–$C_6$)alkenylene" means a linear or branched alkenylene group of 2 to 6 carbon atoms. The term "($C_2$–$C_6$)alkynylene" means a linear or branched alkynylene group of 2 to 6 carbon atoms.

The "fused ring" includes, for example, naphthalene ring, tetrahydronaphthalene ring, indene ring, indane ring, quinoline ring, quinazoline ring, chroman ring, isochroman ring, indole ring, indoline ring, benzodioxane ring, benzodioxole ring, benzofuran ring, dihydrobenzofuran ring, benzothiophene ring, dihydrobenzothiophene ring, benzoxazole ring, benzothiazole ring, benzimidazole ring and indazole ring.

The salts of the sulfonamide derivative represented by general formula (I) of the present invention include, for example, inorganic acid salts such as hydrochloride, sulfate, nitrate, phosphate and the like; organic acid salts such as acetate, fumarate, maleate, oxalate, methanesulfonate, benzenesulfonate, p-toluenesulfonate and the like; and salts with a sodium ion, potassium ion, calcium ion or the like.

The sulfonamide derivative of general formula (I) of the present invention contains one or more asymmetric carbon atoms or asymmetric centers in its structural formula in some cases and has two or more optical isomers and diastereomers in some cases. The present invention also includes all of the individual optical isomers and mixtures consisting of these isomers in any ratio. The sulfonamide derivative of general formula (I) of the present invention has two or more geometrical isomers due to one or more carbon-carbon double bonds or carbon-nitrogen double bonds in its structural formula in some cases. The present invention also includes all of the individual geometrical isomers and mixtures consisting of these isomers in any ratio.

In the sulfonamide derivative of general formula (I) of the present invention, A is particularly preferably a ($C_1$–$C_6$) alkylene group; $R^1$ is preferably a hydrogen atom, a ($C_1$–$C_6$)

alkyl group, a substituted $(C_1-C_6)$alkyl group, a $(C_3-C_6)$ alkenyl group, a $(C_3-C_6)$alkynyl group, a phenyl group or a substituted phenyl group, and is particularly preferably a $(C_1-C_6)$alkyl group, a $(C_1-C_6)$alkylthio$(C_1-C_6)$alkyl group, a $(C_1-C_6)$alkylsulfinyl$(C_1-C_6)$alkyl group or a $(C_1-C_6)$ alkylsulfonyl$(C_1-C_6)$alkyl group; each of $R^2$, $R_3$ and $R^4$ is preferably a hydrogen atom or a $(C_1-C_6)$alkyl group; Q is preferably a carbon atom or a nitrogen atom, particularly preferably a carbon atom; X is preferably a halogen atom, a nitro group, a $(C_1-C_6)$alkyl group, a halo$(C_1-C_6)$alkyl group, a halo$(C_1-C_6)$alkoxy group, a $(C_1-C_6)$alkylcarbonyloxy group, a $(C_1-C_6)$alkylsulfonyloxy group or a halo $(C_1-C_6)$alkylsulfonyloxy group, and is particularly preferably a halogen atom; m is preferably 1 or 2, particularly preferably 1; Y is preferably a halogen atom, a $(C_1-C_6)$alkyl group, a halo$(C_1-C_6)$alkoxy$(C_1-C_6)$alkyl group, a halo $(C_1-C_6)$alkyl group, a hydroxyhalo$(C_1-C_6)$alkyl group, a $(C_1-C_6)$alkoxyhalo$(C_1-C_6)$alkyl group, a halo$(C_1-C_6)$ alkoxyhalo$(C_1-C_6)$alkyl group, a $(C_1-C_6)$alkoxy group or a halo $(C_1-C_6)$alkoxy group, and is particularly preferably a $(C_1-C_6)$alkyl group or a halo$(C_1-C_6)$alkyl group; and n is preferably an integer of 1 to 3, particularly preferably 2.

The sulfonamide derivative of general formula (I) of the present invention can be produced, for example, by any of the production processes schematically shown below, but these processes are not intended in any way to limit the scope of the present invention.

Production Processes

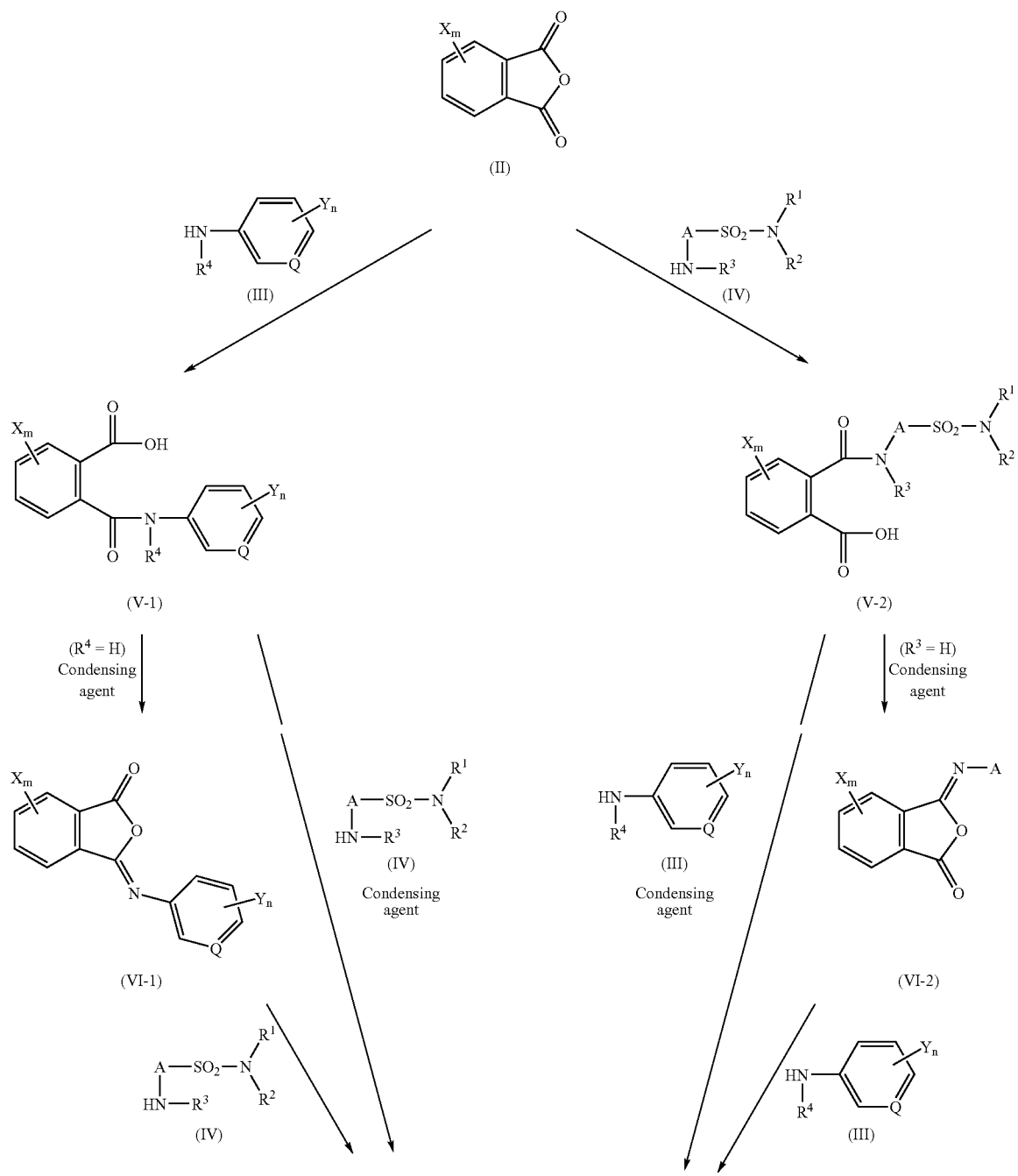

-continued

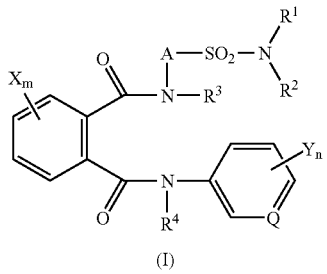

(I)

wherein A, $R^1$ to $R^4$, X, Y, n, m and Q are as defined above.

The production can be carried out by the above reactions according to the process disclosed in J. Med. Chem., 10, 982 (1967), JP-A-11-240857, JP-A-2001-131141 or the like. That is, a phthalic anhydride of general formula (II) is allowed to react with an amine of general formula (III) in the presence of an inert solvent and in the presence or absence of a base or an acid catalyst to obtain a phthalamide of general formula (V-1). When $R^4$ is a hydrogen atom in the phthalamide (V-1), the phthalamide (V-1) is converted to an isoimide derivative of general formula (VI-1) by condensation in the presence of a condensing agent and an inert solvent and in the presence or absence of a base after or without isolating the phthalamide (V-1), and the isoimide derivative (VI-1) is allowed to react with a sulfamoylamine of general formula (IV) in the presence of an inert solvent and in the presence or absence of a base or an acid catalyst after or without isolating the isoimide derivative (VI-1), whereby the sulfonamide derivative of general formula (I) can be produced. When $R^4$ is a substituent other than a hydrogen atom in the phthalamide (V-1), the sulfonamide derivative of general formula (I) can be produced by condensing the phthalamide (V-1) with a sulfamoylamine of general formula (IV) in the presence of a condensing agent and an inert solvent and in the presence or absence of a base after or without isolating the phthalamide (V-1).

In addition, a phthalic anhydride of general formula (II) is allowed to react with a sulfamoylamine of general formula (IV) in the presence of an inert solvent and in the presence or absence of a base or an acid catalyst to obtain a phthalamide of general formula (V-2). When $R^3$ is a hydrogen atom in the phthalamide (V-2), the phthalamide (V-2) is converted to an isoimide derivative of general formula (VI-2) by condensation in the presence of a condensing agent and an inert solvent and in the presence or absence of a base after or without isolating the phthalamide (V-2), and the isoimide derivative (VI-2) is allowed to react with an amine of general formula (III) in the presence of an inert solvent and in the presence or absence of a base or an acid catalyst after or without isolating the isoimide derivative (VI-2), whereby the sulfonamide derivative of general formula (I) can be produced. When $R^3$ is a substituent other than a hydrogen atom in the phthalamide (V-2), the sulfonamide derivative of general formula (I) can be produced by condensing the phthalamide (V-2) with an amine of general formula (III) in the presence of a condensing agent and an inert solvent and in the presence or absence of a base after or without isolating the phthalamide (V-2).

1. General Formula (II)→General Formula (V-1) or General Formula (V-2)

The acid usable in this reaction includes, for example, organic acids such as acetic acid, trifluoroacetic acid, etc.; and inorganic acids such as hydrochloric acid, sulfuric acid, etc. As to the amount of the acid used, the acid may be used in an amount properly chosen in the range of a catalytic amount to excess moles per mole of the phthalic anhydride of general formula (II). The base includes, for example, organic bases such as triethylamine, pyridine, etc.; and inorganic bases such as potassium carbonate, sodium hydrogencarbonate, sodium carbonate, sodium hydroxide, etc. As to the amount of the base used, the base may be used in an amount properly chosen in the range of a catalytic amount to excess moles per mole of the phthalic anhydride of general formula (II).

As the inert solvent used in the reaction, any inert solvent may be used so long as it does not markedly inhibit the progress of the reaction. There can be exemplified inert solvents including, for example, aromatic hydrocarbons such as benzene, toluene, xylene, etc.; halogenated hydrocarbons such as methylene chloride, chloroform, carbon tetrachloride, etc.; halogenated aromatic hydrocarbons such as chlorobenzene, dichlorobenzene, etc.; acyclic or cyclic ethers such as diethyl ether, dioxane, tetrahydrofuran, etc.; esters such as ethyl acetate, etc.; amides such as dimethylformamide, dimethylacetamide, etc,; acids such as acetic acid, etc.; dimethyl sulfoxide; and 1,3-dimethyl-2-imidazolidinone. These inert solvents may be used singly or as a mixture of two or more thereof.

Since the reaction is an equimolar reaction, it is sufficient that the reactants are used in equimolar amounts, though either of them may be used in excess.

As to the reaction temperature, the reaction can be carried out at room temperature to the boiling point of the inert solvent used. Although the reaction time is varied depending on the scale of reaction and the reaction temperature, the reaction may be carried out for a period ranging from several minutes to 48 hours.

After completion of the reaction, the desired compound may be used in the subsequent reaction either after isolation from the reaction system containing the desired compound by a conventional method, or without isolation.

The phthalic anhydride of general formula (II) can be produced by the process described in J. Org. Chem., 52, 129 (1987), J. Am. Chem. Soc., 51, 1865 (1929), J. Am. Chem. Soc., 63, 1542 (1941) or the like.

2. General Formula (V-1) or General Formula (V-2)→General Formula (I)

As the inert solvent used in this reaction, any inert solvent may be used so long as it does not markedly inhibit the progress of the reaction. There can be exemplified inert solvents including, for example, halogenated hydrocarbons such as methylene chloride, chloroform, carbon tetrachloride, etc.; acyclic or cyclic ethers such as diethyl ether, dioxane, tetrahydrofuran, etc.; and nitriles such as acetonitrile, etc. These inert solvents may be used singly or as a mixture of two or more thereof.

As the condensing agent used in the reaction, any condensing agent may be used so long as it is used in conventional amide production. The condensing agent includes, for example, trifluoroacetic anhydride, chlorocarbonates, Mukaiyama reagent (2-chloro-N-methylpyridinium iodide), DCC (1,3-dicyclohexylcarbodiimide), CDI (carbonyl diimidazole) and DEPC (diethyl cyanophosphonate). As to the amount of the condensing agent used, the condensing agent may be used in an amount properly chosen in the range of 1 mole to excess moles per mole of the phthalamide of general formula (V-1) or (V-2).

The base usable in the reaction includes, for example, organic bases such as triethylamine, pyridine, etc.; and inorganic bases such as potassium carbonate, etc. As to the amount of the base used, the base may be used in an amount properly chosen in the range of 1 mole to excess moles per mole of the phthalamide of general formula (V-1) or (V-2).

As to the reaction temperature, the reaction can be carried out at 0° C. to the boiling point of the inert solvent used.

Although the reaction time is varied depending on the scale of reaction and the reaction temperature, the reaction may be carried out for a period ranging from several minutes to 48 hours.

After completion of the reaction, the desired compound is isolated from the reaction system containing the desired compound by a conventional method, and if necessary, purified by recrystallization, column chromatography, etc., whereby the desired compound can be produced.

3. General Formula (V-1)→General Formula (VI-1), or General Formula (V-2)→General Formula (VI-2)

In the case of this reaction, the desired compound can be produced according to, for example, the process described in J. Med. Chem., 10, 982 (1967).

After completion of the reaction, the desired compound may be used in the subsequent reaction either after isolation from the reaction system containing the desired compound by a conventional method, or without isolation.

4. General Formula (VI-1) or General Formula (VI-2) →General Formula (I)

In the case of this reaction, the desired compound can be produced in the same manner as in the item 1.

After completion of the reaction, the desired compound is isolated from the reaction system containing the desired compound by a conventional method, and if necessary, purified by recrystallization, column chromatography, etc., whereby the desired compound can be produced.

The sulfamoylamine (IV) as starting material can be produced according to, for example, any of the processes known in literature and schematically shown below.

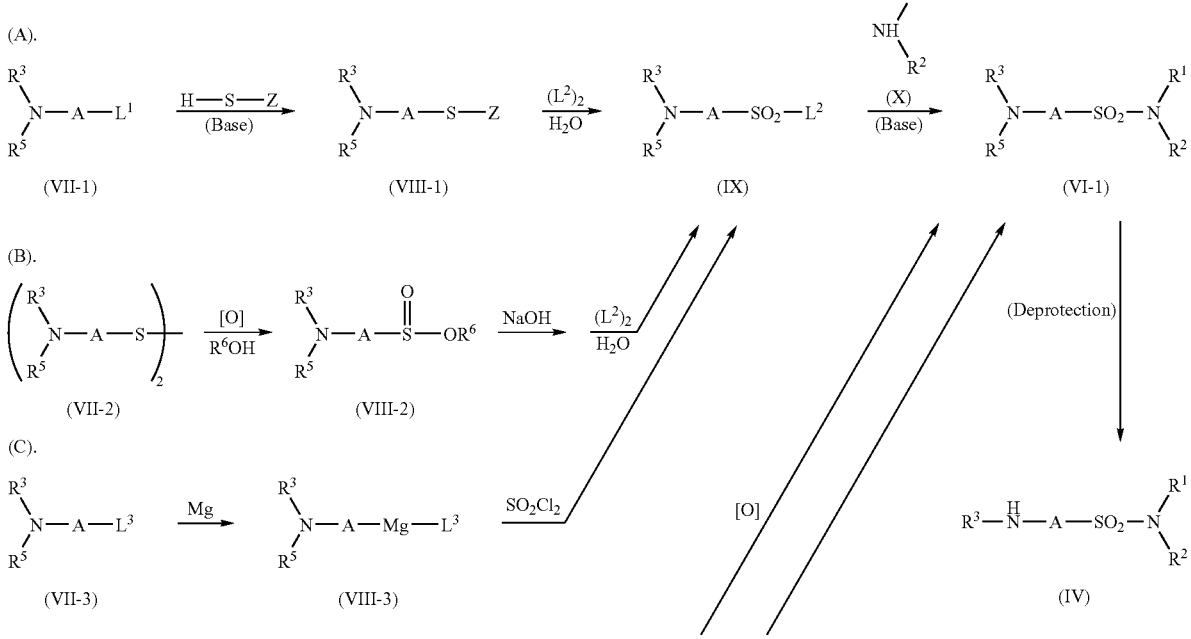

-continued

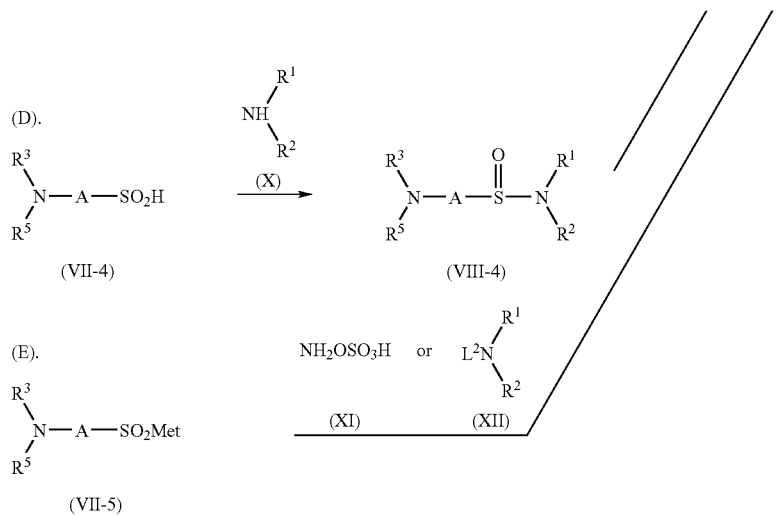

wherein $R^1$, $R^2$, $R^3$ and A are as defined above, $R^5$ is a protecting group such as a benzyloxycarbonyl group, t-butoxycarbonyl group or alkylsilyl group, $R^6$ is a $(C_1-C_6)$alkyl group, each of $L^1$, $L^2$ and $L^3$ is a leaving group such as a halogen atom, Met is a metal atom such as sodium or potassium, and Z is a hydrogen atom, a $(C_1-C_6)$alkyl group or a benzyl group.

(A) General Formula (VII-1)→General Formula (IV)

An amine derivative of general formula (VII-1) is allowed to react with a thiol to obtain a thioalkylamine derivative (VIII-1), according to the method described in J. Am. Chem. Soc., 58, 1348 (1936), J. Am. Chem. Soc., 60, 1486 (1938) or the like. The thioalkylamine derivative is allowed to react with a halogen after or without isolation of the derivative to obtain a sulfonyl halide derivative of general formula (IX). The sulfonyl halide derivative is allowed to react with an amine of general formula (X) to obtain a sulfonamide derivative of general formula (IV-1), according to the method described in Synthesis, 1970, 545, J. Organic Chem., 21, 667 (1956) or the like. The sulfonamide derivative is subjected to deprotection reaction according to a conventional method, whereby the sulfamoylamine of general formula (IV) can be produced.

(B) General Formula (VII-2)→General Formula (IV)

A disulfide derivative of general formula (VII-2) is converted to a sulfenic acid ester derivative (VIII-2) according to the method described in Synth. Commun., 27, 1321 (1997), Synthesis, 1988, 252 or the like. The sulfenic acid ester derivative is hydrolyzed after or without isolation and the hydrolyzate is allowed to react with a halogen according to the method described in J. Am. Chem. Soc., 45, 1068 (1923) or the like to obtain a sulfonyl halide derivative of general formula (IX). Thereafter, the sulfamoylamine of general formula (IV) can be produced in the same manner as in (A).

(C) General Formula (VII-3)→General Formula (IV)

An amine derivative of general formula (VII-3) is converted to a Grignard reagent (VIII-3) according to the method described in J. Org. Chem., 20, 1159 (1955) or the like, and the Grignard reagent (VIII-3) is allowed to react with sulfuryl chloride to obtain a sulfonyl halide derivative of general formula (IX). Thereafter, the sulfamoylamine of general formula (IV) can be produced in the same manner as in (A).

(D) General Formula (VII-4)→General Formula (IV)

A sulfenamide derivative of general formula (VIII-4) is obtained from a sulfenic acid derivative of general formula (VII-4) and an amine derivative of general formula (X) according to the method described in J. Am. Chem. Soc., 57, 2172 (1935), Chem. Lett, 1976, 149 or the like. The sulfenamide derivative is converted to a sulfonamide derivative of general formula (IV-1) according to the method described in J. Org. Chem., 31, 2357 (1966) or the like. Thereafter, the sulfamoylamine of general formula (IV) can be produced by subjecting the sulfonamide derivative to deprotection in the same manner as in (A).

(E) General Formula (VII-5)→General Formula (IV)

As the sulfamoylamine of general formula (IV), a sulfamoylamine in which each of $R^1$ and $R^2$ is a hydrogen atom can be produced by obtaining a sulfonamide derivative of general formula (IV-1) from a sulfenate derivative of general formula (VII-5) and hydroxylamine-O-sulfonic acid (XI) according to the method described in Synthesis, 1985, 1032, and then subjecting the sulfonamide derivative to deprotection in the same manner as in (A). Such a sulfamoylamine of general formula (IV) can be produced also by obtaining a sulfonamide derivative of general formula (IV-1) from a sulfenate derivative of general formula (VII-5) and a N-halo-substituted amine of general formula (XII) accord ing to the method described in J. Org. Chem., 46, 5077 (1981), and then subjecting the sulfonamide derivative to deprotection in the same manner as in (A).

Typical compounds as the sulfonamide derivative of general formula (I) are listed below in Table 1 and Table 2 but they are not intended in any way to limit the scope of the present invention. In the following tables, "n" is a prefix for "normal", "s" is a prefix for "secondary", "t" is a prefix for "tertiary", "i" is a prefix for "iso", "c" is a prefix for "cyclo", and "Me" indicates a methyl group, "Et" an ethyl group, "Pr" a propyl group, "Bu" a butyl group, "Pen" a pentyl group, "Hex" a hexyl group, "Ph" a phenyl group, "Py" a pyridyl group, and "C*" an asymmetric carbon atom. In addition, "$J^1$", "$J^2$" and "$J^3$" indicate the following substituents.

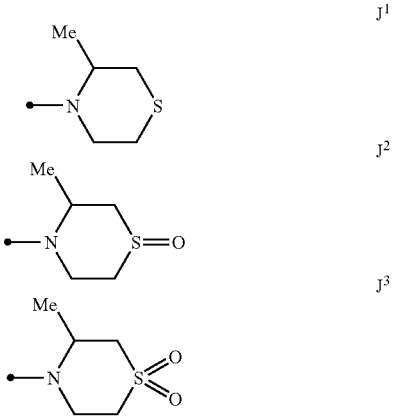

TABLE 1

General formula (I-1)

(I-1)

| No. | —A—SO$_2$NR$^1$R$^2$ | Xm | Yn | Physical property: Melting point ° C. |
|---|---|---|---|---|
| 1-1 | CHMeCH$_2$SO$_2$NH$_2$ | 3-I | 2-Me-4-CF(CF$_3$)$_2$ | 217–219 |
| 1-2 | CHMeCH$_2$SO$_2$NHMe | 3-I | 2-Me-4-CF(CF$_3$)$_2$ | 186–188 |
| 1-3 | CHMeCH$_2$SO$_2$NMe$_2$ | 3-I | 2-Me-4-CF(CF$_3$)$_2$ | 122–125 |
| 1-4 | CHMeCH$_2$SO$_2$NHEt | 3-I | 2-Me-4-CF(CF$_3$)$_2$ | 170–172 |
| 1-5 | CHMeCH$_2$SO$_2$N(Me)Et | 3-I | 2-Me-4-CF(CF$_3$)$_2$ | |
| 1-6 | CHMeCH$_2$SO$_2$NEt$_2$ | 3-I | 2-Me-4-CF(CF$_3$)$_2$ | 116 |
| 1-7 | CHMeCH$_2$SO$_2$NH-n-Pr | 3-I | 2-Me-4-CF(CF$_3$)$_2$ | 147–150 |
| 1-8 | CHMeCH$_2$SO$_2$NH-i-Pr | 3-I | 2-Me-4-CF(CF$_3$)$_2$ | 204–206 |
| 1-9 | CHMeCH$_2$SO$_2$NH-c-Pr | 3-I | 2-Me-4-CF(CF$_3$)$_2$ | |
| 1-10 | CHMeCH$_2$SO$_2$N(n-Pr)$_2$ | 3-I | 2-Me-4-CF(CF$_3$)$_2$ | |
| 1-11 | CHMeCH$_2$SO$_2$N(i-Pr)$_2$ | 3-I | 2-Me-4-CF(CF$_3$)$_2$ | |
| 1-12 | CHMeCH$_2$SO$_2$NH-n-Bu | 3-I | 2-Me-4-CF(CF$_3$)$_2$ | 178–181 |
| 1-13 | CHMeCH$_2$SO$_2$NH-s-Bu | 3-I | 2-Me-4-CF(CF$_3$)$_2$ | |
| 1-14 | CHMeCH$_2$SO$_2$NH-t-Bu | 3-I | 2-Me-4-CF(CF$_3$)$_2$ | 195–197 |
| 1-15 | CHMeCH$_2$SO$_2$NH-i-Bu | 3-I | 2-Me-4-CF(CF$_3$)$_2$ | |
| 1-16 | CHMeCH$_2$SO$_2$NH-c-Bu | 3-I | 2-Me-4-CF(CF$_3$)$_2$ | |
| 1-17 | CHMeCH$_2$SO$_2$NH-c-Pen | 3-I | 2-Me-4-CF(CF$_3$)$_2$ | |
| 1-18 | CHMeCH$_2$SO$_2$NH-c-Hex | 3-I | 2-Me-4-CF(CF$_3$)$_2$ | |
| 1-19 | CHMeCH$_2$SO$_2$NHCH$_2$-c-Pr | 3-I | 2-Me-4-CF(CF$_3$)$_2$ | |
| 1-20 | CHMeCH$_2$SO$_2$NHCH$_2$CH=CH$_2$ | 3-I | 2-Me-4-CF(CF$_3$)$_2$ | 109–113 |
| 1-21 | CHMeCH$_2$SO$_2$NHCH$_2$C≡CH | 3-I | 2-Me-4-CF(CF$_3$)$_2$ | 111–113 |
| 1-22 | CHMeCH$_2$SO$_2$NHCH$_2$Ph | 3-I | 2-Me-4-CF(CF$_3$)$_2$ | 200–202 |
| 1-23 | CHMeCH$_2$SO$_2$NHCH$_2$-(2-F—Ph) | 3-I | 2-Me-4-CF(CF$_3$)$_2$ | 195–198 |
| 1-24 | CHMeCH$_2$SO$_2$NHCH$_2$-(2-Cl—Ph) | 3-I | 2-Me-4-CF(CF$_3$)$_2$ | 193–196 |
| 1-25 | CHMeCH$_2$SO$_2$NHCH$_2$-(2-Br—Ph) | 3-I | 2-Me-4-CF(CF$_3$)$_2$ | 189–192 |
| 1-26 | CHMeCH$_2$SO$_2$NHCH$_2$-(2-Me—Ph) | 3-I | 2-Me-4-CF(CF$_3$)$_2$ | |
| 1-27 | CHMeCH$_2$SO$_2$NHCH$_2$-(2-OMe—Ph) | 3-I | 2-Me-4-CF(CF$_3$)$_2$ | 180–183 |
| 1-28 | CHMeCH$_2$SO$_2$NHCH$_2$-(2-NO$_2$—Ph) | 3-I | 2-Me-4-CF(CF$_3$)$_2$ | 173–177 |
| 1-29 | CHMeCH$_2$SO$_2$NHCH$_2$-(3-OMe—Ph) | 3-I | 2-Me-4-CF(CF$_3$)$_2$ | 196–198 |
| 1-30 | CHMeCH$_2$SO$_2$NHCH$_2$-(3-NO$_2$—Ph) | 3-I | 2-Me-4-CF(CF$_3$)$_2$ | 155–160 |
| 1-31 | CHMeCH$_2$SO$_2$NHCH$_2$-(3-CN—Ph) | 3-I | 2-Me-4-CF(CF$_3$)$_2$ | 147–150 |
| 1-32 | CHMeCH$_2$SO$_2$NHCH$_2$-(2,6-(OMe)$_2$—Ph) | 3-I | 2-Me-4-CF(CF$_3$)$_2$ | 210–213 |
| 1-33 | CHMeCH$_2$SO$_2$NHCH$_2$-(4-Cl—Ph) | 3-I | 2-Me-4-CF(CF$_3$)$_2$ | |
| 1-34 | CHMeCH$_2$SO$_2$NHCH$_2$-(4-Me—Ph) | 3-I | 2-Me-4-CF(CF$_3$)$_2$ | |
| 1-35 | CHMeCH$_2$SO$_2$NHCH$_2$-(4-MeO—Ph) | 3-I | 2-Me-4-CF(CF$_3$)$_2$ | 176–179 |

TABLE 1-continued

General formula (I-1)

$$\text{(I-1)}$$

| No. | —A—SO$_2$NR$^1$R$^2$ | Xm | Yn | Physical property: Melting point ° C. |
|---|---|---|---|---|
| 1-36 | CHMeCH$_2$SO$_2$NHCH$_2$-(4-NO$_2$—Ph) | 3-I | 2-Me-4-CF(CF$_3$)$_2$ | 185–187 |
| 1-37 | CHMeCH$_2$SO$_2$NHCH$_2$-(4-CN—Ph) | 3-I | 2-Me-4-CF(CF$_3$)$_2$ | 169–171 |
| 1-38 | CHMeCH$_2$SO$_2$NHCH$_2$-(4-SCF$_3$—Ph) | 3-I | 2-Me-4-CF(CF$_3$)$_2$ | 201–204 |
| 1-39 | CHMeCH$_2$SO$_2$NHCH$_2$-2-Py | 3-I | 2-Me-4-CF(CF$_3$)$_2$ | 228–231 |
| 1-40 | CHMeCH$_2$SO$_2$NHCH$_2$-3-Py | 3-I | 2-Me-4-CF(CF$_3$)$_2$ | 144–147 |
| 1-41 | CHMeCH$_2$SO$_2$NHCH$_2$-4-Py | 3-I | 2-Me-4-CF(CF$_3$)$_2$ | 166–168 |
| 1-42 | CHMeCH$_2$SO$_2$N(Me)CH$_2$Ph | 3-I | 2-Me-4-CF(CF$_3$)$_2$ | 186–189 |
| 1-43 | CHMeCH$_2$SO$_2$N(Et)CH$_2$Ph | 3-I | 2-Me-4-CF(CF$_3$)$_2$ | 184–186 |
| 1-44 | CHCH$_2$SO$_2$NHCH(Me)Ph | 3-I | 2-Me-4-CF(CF$_3$)$_2$ | 173–175 |
| 1-45 | CHMeCH$_2$SO$_2$NHC*H(Me)Ph R-enantiomer | 3-I | 2-Me-4-CF(CF$_3$)$_2$ | 168–170 |
| 1-46 | CHMeCH$_2$SO$_2$NHC*H(Me)Ph S-enantiomer | 3-I | 2-Me-4-CF(CF$_3$)$_2$ | 159–161 |
| 1-47 | CHMeCH$_2$SO$_2$NHCH$_2$CH$_2$Ph | 3-I | 2-Me-4-CF(CF$_3$)$_2$ | 203–206 |
| 1-48 | CHMeCH$_2$SO$_2$NHC(Me)2CH$_2$Ph | 3-I | 2-Me-4-CF(CF$_3$)$_2$ | 197–198 |
| 1-49 | CHMeCH$_2$SO$_2$N(CH$_2$)$_2$ | 3-I | 2-Me-4-CF(CF$_3$)$_2$ | |
| 1-50 | CHMeCH$_2$SO$_2$N(CH$_2$)$_3$ | 3-I | 2-Me-4-CF(CF$_3$)$_2$ | |
| 1-51 | CHMeCH$_2$SO$_2$N(CH$_2$)$_4$ | 3-I | 2-Me-4-CF(CF$_3$)$_2$ | |
| 1-52 | CHMeCH$_2$SO$_2$N(CH$_2$)$_5$ | 3-I | 2-Me-4-CF(CF$_3$)$_2$ | |
| 1-53 | CHMeCH$_2$SO$_2$N(CH$_2$)$_6$ | 3-I | 2-Me-4-CF(CF$_3$)$_2$ | |
| 1-54 | CHMeCH$_2$SO$_2$N(CH$_2$CH$_2$)$_2$O | 3-I | 2-Me-4-CF(CF$_3$)$_2$ | 204–207 |
| 1-55 | CHMeCH$_2$SO$_2$N(CH$_2$CH$_2$)$_2$S | 3-I | 2-Me-4-CF(CF$_3$)$_2$ | 191–194 |
| 1-56 | CHMeCH$_2$SO$_2$N(CH$_2$CH$_2$)$_2$SO | 3-I | 2-Me-4-CF(CF$_3$)$_2$ | 195–198 |
| 1-57 | CHMeCH$_2$SO$_2$N(CH$_2$CH$_2$)$_2$SO$_2$ | 3-I | 2-Me-4-CF(CF$_3$)$_2$ | 237–240 |
| 1-58 | CMe$_2$CH$_2$SO$_2$N(CH$_2$CH$_2$)$_2$S | 3-I | 2-Me-4-CF(CF$_3$)$_2$ | 164–165 |
| 1-59 | CMe$_2$CH$_2$SO$_2$N(CH$_2$CH$_2$)$_2$SO | 3-I | 2-Me-4-CF(CF$_3$)$_2$ | 167–168 |
| 1-60 | CMe$_2$CH$_2$SO$_2$N(CH$_2$CH$_2$)$_2$SO$_2$ | 3-I | 2-Me-4-CF(CF$_3$)$_2$ | 166–167 |
| 1-61 | CMe$_2$CH$_2$SO$_2$J$^1$ | 3-I | 2-Me-4-CF(CF$_3$)$_2$ | 207–208 |
| 1-62 | CMe$_2$CH$_2$SO$_2$J$^2$ | 3-I | 2-Me-4-CF(CF$_3$)$_2$ | Amorphous |
| 1-63 | CMe$_2$CH$_2$SO$_2$J$^3$ | 3-I | 2-Me-4-CF(CF$_3$)$_2$ | 157–159 |
| 1-64 | CHMeCH$_2$SO$_2$N(CH$_2$CH$_2$)$_2$NH | 3-I | 2-Me-4-CF(CF$_3$)$_2$ | |
| 1-65 | CHMeCH$_2$SO$_2$N(CH$_2$CH$_2$)$_2$NMe | 3-I | 2-Me-4-CF(CF$_3$)$_2$ | |
| 1-66 | CHMeCH$_2$SO$_2$N(CH$_2$CH$_2$)$_2$NOOMe | 3-I | 2-Me-4-CF(CF$_3$)$_2$ | 196–198 |
| 1-67 | CHMeCH$_2$SO$_2$N(CH$_2$CH$_2$)$_2$C=O | 3-I | 2-Me-4-CF(CF$_3$)$_2$ | 209–211 |
| 1-68 | CHMeCH$_2$SO$_2$NHCH$_2$CF$_3$ | 3-I | 2-Me-4-CF(CF$_3$)$_2$ | |
| 1-69 | CHMeCH$_2$SO$_2$NHCH(Me)CF$_3$ | 3-I | 2-Me-4-CF(CF$_3$)$_2$ | |
| 1-70 | CHMeCH$_2$SO$_2$NHCH$_2$CH=OCl$_2$ | 3-I | 2-Me-4-CF(CF$_3$)$_2$ | |
| 1-71 | CHMeCH$_2$SO$_2$NH(CH$_2$)$_2$Cl | 3-I | 2-Me-4-CF(CF$_3$)$_2$ | 90–95 |
| 1-72 | CHMeCH$_2$SO$_2$NH(CH$_2$)$_2$OH | 3-I | 2-Me-4-CF(CF$_3$)$_2$ | 171–174 |
| 1-73 | CHMeCH$_2$SO$_2$NH(CH$_2$)$_2$OMe | 3-I | 2-Me-4-CF(CF$_3$)$_2$ | 142–144 |
| 1-74 | CHMeCH$_2$SO$_2$NHCHMeCH$_2$OMe | 3-I | 2-Me-4-CF(CF$_3$)$_2$ | |
| 1-75 | CHMeCH$_2$SO$_2$NH(CH$_2$)$_2$SMe | 3-I | 2-Me-4-CF(CF$_3$)$_2$ | 156–158 |
| 1-76 | CHMeCH$_2$SO$_2$NH(CH$_2$)$_2$SOMe | 3-I | 2-Me-4-CF(CF$_3$)$_2$ | 132–134 |
| 1-77 | CHMeCH$_2$SO$_2$NH(CH$_2$)$_2$SO$_2$Me | 3-I | 2-Me-4-CF(CF$_3$)$_2$ | 186–189 |
| 1-78 | OMe$_2$CH$_2$SO$_2$NH(CH$_2$)$_2$OH | 3-I | 2-Me-4-CF(CF$_3$)$_2$ | 150–151 |
| 1-79 | OMe$_2$CH$_2$SO$_2$NH(CH$_2$)$_2$OMe | 3-I | 2-Me-4-CF(CF$_3$)$_2$ | 167–168 |
| 1-80 | OMe$_2$CH$_2$SO$_2$NH(CH$_2$)$_2$OOOMe | 3-I | 2-Me-4-CF(CF$_3$)$_2$ | 181–182 |
| 1-81 | OMe$_2$CH$_2$SO$_2$NH(CH$_2$)$_2$SMe | 3-I | 2-Me-4-CF(CF$_3$)$_2$ | 161–162 |
| 1-82 | OMe$_2$CH$_2$SO$_2$NH(CH$_2$)$_2$SOMe | 3-I | 2-Me-4-CF(CF$_3$)$_2$ | 154–155 |
| 1-83 | OMe$_2$CH$_2$SO$_2$NH(CH$_2$)$_2$SO$_2$Me | 3-I | 2-Me-4-CF(CF$_3$)$_2$ | 151–152 |
| 1-84 | OMe$_2$CH$_2$SO$_2$NH(CH$_2$)$_2$SEt | 3-I | 2-Me-4-CF(CF$_3$)$_2$ | 166–167 |
| 1-85 | OMe$_2$CH$_2$SO$_2$NH(CH$_2$)$_2$SOEt | 3-I | 2-Me-4-CF(CF$_3$)$_2$ | 144–145 |
| 1-86 | OMe$_2$CH$_2$SO$_2$NH(CH$_2$)$_2$SO$_2$Et | 3-I | 2-Me-4-CF(CF$_3$)$_2$ | 168–169 |
| 1-87 | OMe$_2$CH$_2$SO$_2$NH(CH$_2$)$_2$SPh | 3-I | 2-Me-4-CF(CF$_3$)$_2$ | 155–156 |
| 1-88 | OMe$_2$CH$_2$SO$_2$NH(CH$_2$)$_2$SOPh | 3-I | 2-Me-4-CF(CF$_3$)$_2$ | 151–153 |
| 1-89 | OMe$_2$CH$_2$SO$_2$NH(CH$_2$)$_2$SO$_2$Ph | 3-I | 2-Me-4-CF(CF$_3$)$_2$ | 170–172 |
| 1-90 | OMe$_2$CH$_2$SO$_2$NH(CH$_2$)$_2$NMe$_2$ | 3-I | 2-Me-4-CF(CF$_3$)$_2$ | |
| 1-91 | CHMeCH$_2$SO$_2$NHCHMeCH$_2$SMe | 3-I | 2-Me-4-CF(CF$_3$)$_2$ | 190–193 |
| 1-92 | CHMeCH$_2$SO$_2$NHCHMeCH$_2$SOMe | 3-I | 2-Me-4-CF(CF$_3$)$_2$ | 130–133 |

TABLE 1-continued

General formula (I-1)

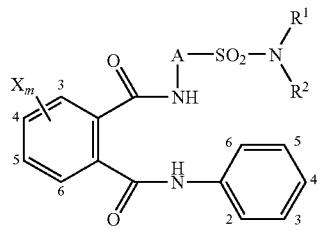

(I-1)

| No. | —A—SO$_2$NR$^1$R$^2$ | Xm | Yn | Physical property: Melting point ° C. |
|---|---|---|---|---|
| 1-93 | CHMeCH$_2$SO$_2$NHCHMeCH$_2$SO$_2$Me | 3-I | 2-Me-4-CF(CF$_3$)$_2$ | 150–154 |
| 1-94 | CHMeCH$_2$SO$_2$NOMe$_2$CH$_2$SMe | 3-I | 2-Me-4-CF(CF$_3$)$_2$ | 157–160 |
| 1-95 | CHMeCH$_2$SO$_2$NH(CH$_2$)$_3$OMe | 3-I | 2-Me-4-CF(CF$_3$)$_2$ | |
| 1-96 | OMe$_2$CH$_2$SO$_2$NH(CH$_2$)$_3$SMe | 3-I | 2-Me-4-CF(CF$_3$)$_2$ | |
| 1-97 | OMe$_2$CH$_2$SO$_2$NH(CH$_2$)$_3$SOMe | 3-I | 2-Me-4-CF(CF$_3$)$_2$ | |
| 1-98 | OMe$_2$CH$_2$SO$_2$NH(CH$_2$)$_3$SO$_2$Me | 3-I | 2-Me-4-CF(CF$_3$)$_2$ | |
| 1-99 | CHMeCH$_2$SO$_2$NHCH$_2$CN | 3-I | 2-Me-4-CF(CF$_3$)$_2$ | |
| 1-100 | CHMeCH$_2$SO$_2$NHCH$_2$CO$_2$Me | 3-I | 2-Me-4-CF(CF$_3$)$_2$ | |
| 1-101 | CHMeCH$_2$SO$_2$NHCH$_2$CO$_2$Et | 3-I | 2-Me-4-CF(CF$_3$)$_2$ | |
| 1-102 | CHMeCH$_2$SO$_2$NHCHMeCO$_2$Me | 3-I | 2-Me-4-CF(CF$_3$)$_2$ | |
| 1-103 | CHMeCH$_2$SO$_2$NHCHMeCONH$_2$ | 3-I | 2-Me-4-CF(CF$_3$)$_2$ | 228–230 |
| 1-104 | CHMeCH$_2$SO$_2$NHCHMeCONHEt | 3-I | 2-Me-4-CF(CF$_3$)$_2$ | 176–177 |
| 1-105 | CHMeCH$_2$SO$_2$NHCH$_2$CONEt$_2$ | 3-I | 2-Me-4-CF(CF$_3$)$_2$ | 172–174 |
| 1-106 | CHMeCH$_2$SO$_2$NHPh | 3-I | 2-Me-4-CF(CF$_3$)$_2$ | 232–234 |
| 1-107 | CHMeCH$_2$SO$_2$NH(2-F—Ph) | 3-I | 2-Me-4-CF(CF$_3$)$_2$ | 211–212 |
| 1-108 | CHMeCH$_2$SO$_2$NH(2-MeO—Ph) | 3-I | 2-Me-4-CF(CF$_3$)$_2$ | 101–106 |
| 1-109 | CHMeCH$_2$SO$_2$NH(3-F—Ph) | 3-I | 2-Me-4-CF(CF$_3$)$_2$ | 235–236 |
| 1-110 | CHMeCH$_2$SO$_2$NH(4-F—Ph) | 3-I | 2-Me-4-CF(CF$_3$)$_2$ | 228–233 |
| 1-111 | CHMeCH$_2$SO$_2$NH(4-MeO—Ph) | 3-I | 2-Me-4-CF(CF$_3$)$_2$ | 143–147 |
| 1-112 | CHMeCH$_2$SO$_2$NH(4-MeS—Ph) | 3-I | 2-Me-4-CF(CF$_3$)$_2$ | 165–170 |
| 1-113 | CHMeCH$_2$SO$_2$NH-2-Py | 3-I | 2-Me-4-CF(CF$_3$)$_2$ | |
| 1-114 | CHMeCH$_2$SO$_2$NH-3-Py | 3-I | 2-Me-4-CF(CF$_3$)$_2$ | |
| 1-115 | CHMeCH$_2$SO$_2$NHOH | 3-I | 2-Me-4-CF(CF$_3$)$_2$ | |
| 1-116 | CHMeCH$_2$SO$_2$NHOMe | 3-I | 2-Me-4-CF(CF$_3$)$_2$ | 200–205 |
| 1-117 | CHMeCH$_2$SO$_2$NMeOMe | 3-I | 2-Me-4-CF(CF$_3$)$_2$ | |
| 1-118 | CHMeCH$_2$SO$_2$NHNH$_2$ | 3-I | 2-Me-4-CF(CF$_3$)$_2$ | |
| 1-119 | CHMeCH$_2$SO$_2$NMeNH$_2$ | 3-I | 2-Me-4-CF(CF$_3$)$_2$ | |
| 1-120 | CHMeCH$_2$SO$_2$NMeNHMe | 3-I | 2-Me-4-CF(CF$_3$)$_2$ | |
| 1-121 | CHMeCH$_2$SO$_2$NHMe$_2$ | 3-I | 2-Me-4-CF(CF$_3$)$_2$ | 161–166 |
| 1-122 | CHMeCH$_2$SO$_2$NHNHPh | 3-I | 2-Me-4-CF(CF$_3$)$_2$ | |
| 1-123 | CHMeCH$_2$SO$_2$NHNHOOMe | 3-I | 2-Me-4-CF(CF$_3$)$_2$ | |
| 1-124 | CHMeCH$_2$SO$_2$NHNHOOPh | 3-I | 2-Me-4-CF(CF$_3$)$_2$ | |
| 1-125 | CHMeCH$_2$SO$_2$NHN=CHMe$_2$ | 3-I | 2-Me-4-CF(CF$_3$)$_2$ | |
| 1-126 | CHMeCH$_2$SO$_2$NHN=CHPh | 3-I | 2-Me-4-CF(CF$_3$)$_2$ | |
| 1-127 | CHMeCH$_2$SO$_2$NHN=C(Me)Ph | 3-I | 2-Me-4-CF(CF$_3$)$_2$ | |
| 1-128 | CHMeCH$_2$SO$_2$N=CHMe | 3-I | 2-Me-4-CF(CF$_3$)$_2$ | |
| 1-129 | CHMeCH$_2$SO$_2$N=CHEt | 3-I | 2-Me-4-CF(CF$_3$)$_2$ | |
| 1-130 | CHMeCH$_2$SO$_2$N=CH-i-Pr | 3-I | 2-Me-4-CF(CF$_3$)$_2$ | |
| 1-131 | CHMeCH$_2$SO$_2$N=CHPh | 3-I | 2-Me-4-CF(CF$_3$)$_2$ | |
| 1-132 | CHMeCH$_2$SO$_2$N=CHNHMe | 3-I | 2-Me-4-CF(CF$_3$)$_2$ | |
| 1-133 | CHMeCH$_2$SO$_2$N=CHNMe$_2$ | 3-I | 2-Me-4-CF(CF$_3$)$_2$ | |
| 1-134 | CHMeCH$_2$SO$_2$N=CHNEt$_2$ | 3-I | 2-Me-4-CF(CF$_3$)$_2$ | |
| 1-135 | C*HMeCH$_2$SO$_2$NH$_2$ R-enantiomer | 3-I | 2-Me-4-CF(CF$_3$)$_2$ | |
| 1-136 | C*HMeCH$_2$SO$_2$NH$_2$ S-enantiomer | 3-I | 2-Me-4-CF(CF$_3$)$_2$ | |
| 1-137 | C*HMeCH$_2$SO$_2$NHMe R-enantiomer | 3-I | 2-Me-4-CF(CF$_3$)$_2$ | |
| 1-138 | C*HMeCH$_2$SO$_2$NHMe S-enantiomer | 3-I | 2-Me-4-CF(CF$_3$)$_2$ | |
| 1-139 | C*HMeCH$_2$SO$_2$NMe$_2$ R-enantiomer | 3-I | 2-Me-4-CF(CF$_3$)$_2$ | |
| 1-140 | C*HMeCH$_2$SO$_2$NMe$_2$ S-enantiomer | 3-I | 2-Me-4-CF(CF$_3$)$_2$ | |
| 1-141 | C*HMeCH$_2$SO$_2$NHEt R-enantiomer | 3-I | 2-Me-4-CF(CF$_3$)$_2$ | |
| 1-142 | C*HMeCH$_2$SO$_2$NHEt S-enantiomer | 3-I | 2-Me-4-CF(CF$_3$)$_2$ | 105–107 |
| 1-143 | C*HMeCH$_2$SO$_2$NEt$_2$ | 3-I | 2-Me-4-CF(CF$_3$)$_2$ | |

TABLE 1-continued

General formula (I-1)

$$(I-1)$$

| No. | —A—SO$_2$NR$^1$R$^2$ | Xm | Yn | Physical property: Melting point ° C. |
|---|---|---|---|---|
| 1-144 | C*HMeCH$_2$SO$_2$NEt$_2$ R-enantiomer | 3-I | 2-Me-4-CF(CF$_3$)$_2$ | 159–163 |
| 1-145 | C*HMeCH$_2$SO$_2$NHCH$_2$Ph S-enantiomer | 3-I | 2-Me-4-CF(CF$_3$)$_2$ | |
| 1-146 | C*HMeCH$_2$SO$_2$NHCH$_2$Ph R-enantiomer | 3-I | 2-Me-4-CF(CF$_3$)$_2$ | 158–159 |
| 1-147 | C*HMeCH$_2$SO$_2$NHC*HMeCH$_2$SMe S,S-enantiomer | 3-I | 2-Me-4-CF(CF$_3$)$_2$ | Amorphous |
| 1-148 | C*HMeCH$_2$SO$_2$NHC*HMeCH$_2$SOMe S,S-enantiomer | 3-I | 2-Me-4-CF(CF$_3$)$_2$ | 115–120 |
| 1-149 | C*HMeCH$_2$SO$_2$NHC*HMeCH$_2$SO$_2$Me S,S-enantiomer | 3-I | 2-Me-4-CF(CF$_3$)$_2$ | Amorphous |
| 1-150 | CHMeSO$_2$NH$_2$ | 3-I | 2-Me-4-CF(CF$_3$)$_2$ | |
| 1-151 | CHMeSO$_2$NHMe | 3-I | 2-Me-4-CF(CF$_3$)$_2$ | |
| 1-152 | CHMeSO$_2$NMe$_2$ | 3-I | 2-Me-4-CF(CF$_3$)$_2$ | |
| 1-153 | CHMeSO$_2$NHEt | 3-I | 2-Me-4-CF(CF$_3$)$_2$ | |
| 1-154 | CHMeSO$_2$NEt$_2$ | 3-I | 2-Me-4-CF(CF$_3$)$_2$ | |
| 1-155 | CHMe(CH$_2$)$_2$SO$_2$NH$_2$ | 3-I | 2-Me-4-CF(CF$_3$)$_2$ | |
| 1-156 | CHMe(CH$_2$)$_2$SO$_2$NHMe | 3-I | 2-Me-4-CF(CF$_3$)$_2$ | |
| 1-157 | CHMe(CH$_2$)$_2$SO$_2$NMe$_2$ | 3-I | 2-Me-4-CF(CF$_3$)$_2$ | |
| 1-158 | CHMe(CH$_2$)$_2$SO$_2$NHEt | 3-I | 2-Me-4-CF(CF$_3$)$_2$ | |
| 1-159 | CHMe(CH$_2$)$_2$SO$_2$NEt$_2$ | 3-I | 2-Me-4-CF(CF$_3$)$_2$ | |
| 1-160 | CHMe(CH$_2$)$_2$SO$_2$NH$_2$ S-enantiomer | 3-I | 2-Me-4-CF(CF$_3$)$_2$ | |
| 1-161 | C*HMe(CH$_2$)$_2$SO$_2$NHMe S-enantiomer | 3-I | 2-Me-4-CF(CF$_3$)$_2$ | |
| 1-162 | C*HMe(CH$_2$)$_2$SO$_2$NMe$_2$ S-enantiomer | 3-I | 2-Me-4-CF(CF$_3$)$_2$ | |
| 1-163 | C*HMe(CH$_2$)$_2$SO$_2$NHEt S-enantiomer | 3-I | 2-Me-4-CF(CF$_3$)$_2$ | |
| 1-164 | C*HMe(CH$_2$)$_2$SO$_2$NEt$_2$ S-enantiomer | 3-I | 2-Me-4-CF(CF$_3$)$_2$ | |
| 1-165 | CHMe(CH$_2$)$_3$SO$_2$NH$_2$ | 3-I | 2-Me-4-CF(CF$_3$)$_2$ | |
| 1-166 | CHMe(CH$_2$)$_3$SO$_2$NHMe | 3-I | 2-Me-4-CF(CF$_3$)$_2$ | |
| 1-167 | CHMe(CH$_2$)$_3$SO$_2$NMe$_2$ | 3-I | 2-Me-4-CF(CF$_3$)$_2$ | |
| 1-168 | CHMe(CH$_2$)$_3$SO$_2$NHEt | 3-I | 2-Me-4-CF(CF$_3$)$_2$ | |
| 1-169 | CHMe(CH$_2$)$_3$SO$_2$NEt$_2$ | 3-I | 2-Me-4-CF(CF$_3$)$_2$ | |
| 1-170 | CHMe(CH$_2$)$_4$SO$_2$NH$_2$ | 3-I | 2-Me-4-CF(CF$_3$)$_2$ | |
| 1-171 | CHMe(CH$_2$)$_4$SO$_2$NHMe | 3-I | 2-Me-4-CF(CF$_3$)$_2$ | |
| 1-172 | CHMe(CH$_2$)$_4$SO$_2$NMe$_2$ | 3-I | 2-Me-4-CF(CF$_3$)$_2$ | |
| 1-173 | CHMe(CH$_2$)$_4$SO$_2$NHEt | 3-I | 2-Me-4-CF(CF$_3$)$_2$ | |
| 1-174 | CHMe(CH$_2$)$_4$SO$_2$NEt$_2$ | 3-I | 2-Me-4-CF(CF$_3$)$_2$ | |
| 1-175 | OMe$_2$CH$_2$SO$_2$NH$_2$ | 3-I | 2-Me-4-CF(CF$_3$)$_2$ | Amorphous |
| 1-176 | OMe$_2$CH$_2$SO$_2$NHMe | 3-I | 2-Me-4-CF(CF$_3$)$_2$ | Amorphous |
| 1-177 | OMe$_2$CH$_2$SO$_2$NMe$_2$ | 3-I | 2-Me-4-CF(CF$_3$)$_2$ | 151–152 |
| 1-178 | OMe$_2$CH$_2$SO$_2$NHEt | 3-I | 2-Me-4-CF(CF$_3$)$_2$ | Amorphous |
| 1-179 | OMe$_2$CH$_2$SO$_2$NEt$_2$ | 3-I | 2-Me-4-CF(CF$_3$)$_2$ | Amorphous |
| 1-180 | OMe$_2$CH$_2$SO$_2$NH-n-Bu | 3-I | 2-Me-4-CF(CF$_3$)$_2$ | 185–186 |
| 1-181 | OMe$_2$CH$_2$SO$_2$N(CH$_2$)$_4$ | 3-I | 2-Me-4-CF(CF$_3$)$_2$ | 129–130 |
| 1-182 | OMe$_2$CH$_2$SO$_2$NHCH$_2$CH=CH$_2$ | 3-I | 2-Me-4-CF(CF$_3$)$_2$ | |
| 1-183 | OMe$_2$CH$_2$SO$_2$NHCH$_2$C≡CH | 3-I | 2-Me-4-CF(CF$_3$)$_2$ | |
| 1-184 | OMe$_2$CH$_2$SO$_2$NHCH$_2$Ph | 3-I | 2-Me-4-CF(CF$_3$)$_2$ | 152–153 |
| 1-185 | OMe$_2$CH$_2$SO$_2$NHPh | 3-I | 2-Me-4-CF(CF$_3$)$_2$ | |
| 1-186 | OMe$_2$CH$_2$SO$_2$NH-2-Py | 3-I | 2-Me-4-CF(CF$_3$)$_2$ | |
| 1-187 | OMe$_2$SO$_2$NH$_2$ | 3-I | 2-Me-4-CF(CF$_3$)$_2$ | |
| 1-188 | OMe$_2$SO$_2$NHMe | 3-I | 2-Me-4-CF(CF$_3$)$_2$ | |
| 1-189 | OMe$_2$SO$_2$NMe$_2$ | 3-I | 2-Me-4-CF(CF$_3$)$_2$ | |
| 1-190 | OMe$_2$SO$_2$NHEt | 3-I | 2-Me-4-CF(CF$_3$)$_2$ | |

TABLE 1-continued

General formula (I-1)

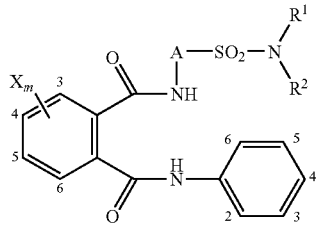

(I-1)

| No. | —A—SO$_2$NR$^1$R$^2$ | Xm | Yn | Physical property: Melting point ° C. |
|---|---|---|---|---|
| 1-191 | OMe$_2$SO$_2$NEt$_2$ | 3-I | 2-Me-4-CF(CF$_3$)$_2$ | |
| 1-192 | OMe$_2$(CH$_2$)$_2$SO$_2$NH$_2$ | 3-I | 2-Me-4-CF(CF$_3$)$_2$ | |
| 1-193 | OMe$_2$(CH$_2$)$_2$SO$_2$NHMe | 3-I | 2-Me-4-CF(CF$_3$)$_2$ | |
| 1-194 | OMe$_2$(CH$_2$)$_2$SO$_2$NMe$_2$ | 3-I | 2-Me-4-CF(CF$_3$)$_2$ | |
| 1-195 | OMe$_2$(CH$_2$)$_2$SO$_2$NHEt | 3-I | 2-Me-4-CF(CF$_3$)$_2$ | |
| 1-196 | OMe$_2$(CH$_2$)$_2$SO$_2$NEt$_2$ | 3-I | 2-Me-4-CF(CF$_3$)$_2$ | |
| 1-197 | OMe$_2$(CH$_2$)$_3$SO$_2$NH$_2$ | 3-I | 2-Me-4-CF(CF$_3$)$_2$ | |
| 1-198 | OMe$_2$(CH$_2$)$_3$SO$_2$NHMe | 3-I | 2-Me-4-CF(CF$_3$)$_2$ | |
| 1-199 | OMe$_2$(CH$_2$)$_3$SO$_2$NMe$_2$ | 3-I | 2-Me-4-CF(CF$_3$)$_2$ | |
| 1-200 | OMe$_2$(CH$_2$)$_3$SO$_2$NHEt | 3-I | 2-Me-4-CF(CF$_3$)$_2$ | 185–186 |
| 1-201 | OMe$_2$(CH$_2$)$_3$SO$_2$NEt$_2$ | 3-I | 2-Me-4-CF(CF$_3$)$_2$ | 142–145 |
| 1-202 | OMe$_2$(CH$_2$)$_4$SO$_2$NH$_2$ | 3-I | 2-Me-4-CF(CF$_3$)$_2$ | |
| 1-203 | OMe$_2$(CH$_2$)$_4$SO$_2$NHMe | 3-I | 2-Me-4-CF(CF$_3$)$_2$ | |
| 1-204 | OMe$_2$(CH$_2$)$_4$SO$_2$NMe$_2$ | 3-I | 2-Me-4-CF(CF$_3$)$_2$ | |
| 1-205 | OMe$_2$(CH$_2$)$_4$SO$_2$NHEt | 3-I | 2-Me-4-CF(CF$_3$)$_2$ | |
| 1-206 | OMe$_2$(CH$_2$)$_4$SO$_2$NEt$_2$ | 3-I | 2-Me-4-CF(CF$_3$)$_2$ | |
| 1-207 | CHMeCH$_2$SO$_2$NHEt | H | 2-Me-4-CF(CF$_3$)$_2$ | 120–121 |
| 1-208 | OMe$_2$CH$_2$SO$_2$NEt$_2$ | H | 2-Me-4-CF(CF$_3$)$_2$ | 93–94 |
| 1-209 | CHMeCH$_2$SO$_2$NHEt | 3-F | 2-Me-4-CF(CF$_3$)$_2$ | |
| 1-210 | CHMeCH$_2$SO$_2$NHEt | 3-Cl | 2-Me-4-CF(CF$_3$)$_2$ | |
| 1-211 | CHMeCH$_2$SO$_2$NEt$_2$ | 3-Cl | 2-Me-4-CF(CF$_3$)$_2$ | 103–108 |
| 1-212 | CHMeCH$_2$SO$_2$NHEt | 3-Br | 2-Me-4-CF(CF$_3$)$_2$ | 136–138 |
| 1-213 | CHMeCH$_2$SO$_2$NMe$_2$ | 3-Br | 2-Me-4-CF(CF$_3$)$_2$ | 107–110 |
| 1-214 | CHMeCH$_2$SO$_2$NEt$_2$ | 3-Br | 2-Me-4-CF(CF$_3$)$_2$ | 112–115 |
| 1-215 | CHMeCH$_2$SO$_2$NH-n-Pr | 3-Br | 2-Me-4-CF(CF$_3$)$_2$ | 159–161 |
| 1-216 | CHMeCH$_2$SO$_2$NH-i-Pr | 3-Br | 2-Me-4-CF(CF$_3$)$_2$ | 185–187 |
| 1-217 | CHMeCH$_2$SO$_2$NH-n-Bu | 3-Br | 2-Me-4-CF(CF$_3$)$_2$ | 179–181 |
| 1-218 | CHMeCH$_2$SO$_2$NHCH$_2$Ph | 3-Br | 2-Me-4-CF(CF$_3$)$_2$ | 139–141 |
| 1-219 | OMe$_2$CH$_2$SO$_2$NEt$_2$ | 3-Br | 2-Me-4-CF(CF$_3$)$_2$ | 169–170 |
| 1-220 | CHMeCH$_2$SO$_2$NHEt | 3,4-Cl$_2$ | 2-Me-4-CF(CF$_3$)$_2$ | |
| 1-221 | CHMeCH$_2$SO$_2$NHEt | 3,4-Br$_2$ | 2-Me-4-CF(CF$_3$)$_2$ | |
| 1-222 | CHMeCH$_2$SO$_2$NHEt | 4-Cl | 2-Me-4-CF(CF$_3$)$_2$ | |
| 1-223 | CHMeCH$_2$SO$_2$NHEt | 4-Br | 2-Me-4-CF(CF$_3$)$_2$ | |
| 1-224 | CHMeCH$_2$SO$_2$NHEt | 4-I | 2-Me-4-CF(CF$_3$)$_2$ | |
| 1-225 | CHMeCH$_2$SO$_2$NHEt | 3-NO$_2$ | 2-Me-4-CF(CF$_3$)$_2$ | |
| 1-226 | CHMeCH$_2$SO$_2$NHEt | 3-NH$_2$ | 2-Me-4-CF(CF$_3$)$_2$ | |
| 1-227 | CHMeCH$_2$SO$_2$NHEt | 3-N(CH$_3$)$_2$ | 2-Me-4-CF(CF$_3$)$_2$ | |
| 1-228 | CHMeCH$_2$SO$_2$NHEt | 3-NHCOCH$_3$ | 2-Me-4-CF(CF$_3$)$_2$ | |
| 1-229 | CHMeCH$_2$SO$_2$NHEt | 3-NHCOCF$_3$ | 2-Me-4-CF(CF$_3$)$_2$ | |
| 1-230 | CHMeCH$_2$SO$_2$NHEt | 3-NHSO$_2$CH$_3$ | 2-Me-4-CF(CF$_3$)$_2$ | |
| 1-231 | CHMeCH$_2$SO$_2$NHEt | 3-NHSO$_2$CF$_3$ | 2-Me-4-CF(CF$_3$)$_2$ | |
| 1-232 | CHMeCH$_2$SO$_2$NHEt | 3-CH$_3$ | 2-Me-4-CF(CF$_3$)$_2$ | |
| 1-233 | CHMeCH$_2$SO$_2$NHEt | 3-CF$_3$ | 2-Me-4-CF(CF$_3$)$_2$ | |
| 1-234 | CHMeCH$_2$SO$_2$NHEt | 3-OCH$_3$ | 2-Me-4-CF(CF$_3$)$_2$ | |
| 1-235 | CHMeCH$_2$SO$_2$NHEt | 3-OCF$_3$ | 2-Me-4-CF(CF$_3$)$_2$ | |
| 1-236 | CHMeCH$_2$SO$_2$NHEt | 3-OCOCH$_3$ | 2-Me-4-CF(CF$_3$)$_2$ | |
| 1-237 | CHMeCH$_2$SO$_2$NHEt | 3-OCOCF$_3$ | 2-Me-4-CF(CF$_3$)$_2$ | |
| 1-238 | CHMeCH$_2$SO$_2$NHEt | 3-SCH$_3$ | 2-Me-4-CF(CF$_3$)$_2$ | |
| 1-239 | CHMeCH$_2$SO$_2$NHEt | 3-SOCH$_3$ | 2-Me-4-CF(CF$_3$)$_2$ | |
| 1-240 | CHMeCH$_2$SO$_2$NHEt | 3-SO$_2$CH$_3$ | 2-Me-4-CF(CF$_3$)$_2$ | |
| 1-241 | CHMeCH$_2$SO$_2$NHEt | 3-SCF$_3$ | 2-Me-4-CF(CF$_3$)$_2$ | |
| 1-242 | CHMeCH$_2$SO$_2$NHEt | 3-SOCF$_3$ | 2-Me-4-CF(CF$_3$)$_2$ | |
| 1-243 | CHMeCH$_2$SO$_2$NHEt | 3-SO$_2$CF$_3$ | 2-Me-4-CF(CF$_3$)$_2$ | |
| 1-244 | CHMeCH$_2$SO$_2$NHEt | 3-OSO$_2$CH$_3$ | 2-Me-4-CF(CF$_3$)$_2$ | |
| 1-245 | CHMeCH$_2$SO$_2$NHEt | 3-OSO$_2$CF$_3$ | 2-Me-4-CF(CF$_3$)$_2$ | |
| 1-246 | CHMeCH$_2$SO$_2$NHEt | 3-C≡CH | 2-Me-4-CF(CF$_3$)$_2$ | |
| 1-247 | CHMeCH$_2$SO$_2$NHEt | 3-C≡CCF$_3$ | 2-Me-4-CF(CF$_3$)$_2$ | |
| 1-248 | CHMeCH$_2$SO$_2$NHEt | 3-CN | 2-Me-4-CF(CF$_3$)$_2$ | |
| 1-249 | CHMeCH$_2$SO$_2$NHEt | 3-CHCHCHCH-4 | 2-Me-4-CF(CF$_3$)$_2$ | |

TABLE 1-continued

General formula (I-1)

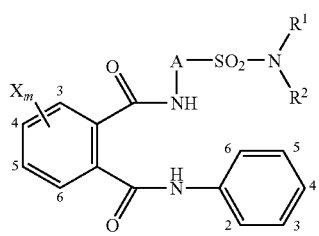

(I-1)

| No. | —A—SO$_2$NR$^1$R$^2$ | Xm | Yn | Physical property: Melting point ° C. |
|---|---|---|---|---|
| 1-250 | CHMeCH$_2$SO$_2$NHEt | 3-OCF$_2$O-4 | 2-Me-4-CF(CF$_3$)$_2$ | |
| 1-251 | CHMeCH$_2$SO$_2$NHEt | 3-OCF$_2$CF$_2$O-4 | 2-Me-4-CF(CF$_3$)$_2$ | |
| 1-252 | CHMeCH$_2$SO$_2$NHEt | 3-I | 2-Me-4-F | |
| 1-253 | CHMeCH$_2$SO$_2$NHEt | 3-I | 2-Me-4-Cl | |
| 1-254 | CHMeCH$_2$SO$_2$NHEt | 3-I | 2-Me-4-Br | |
| 1-255 | CHMeCH$_2$SO$_2$NHEt | 3-I | 2-Me-4-I | |
| 1-256 | CHMeCH$_2$SO$_2$NHEt | 3-I | 2-Me-3-F-4-Cl | |
| 1-257 | CHMeCH$_2$SO$_2$NHEt | 3-I | 2-Me-3-Cl-4-F | |
| 1-258 | CHMeCH$_2$SO$_2$NHEt | 3-I | 2-Me-3,4-Cl$_2$ | |
| 1-259 | CHMeCH$_2$SO$_2$NHEt | 3-I | 2-Me-3-Cl-4-Br | |
| 1-260 | CHMeCH$_2$SO$_2$NHEt | 3-I | 2-Me-3-Cl-4-I | |
| 1-261 | CHMeCH$_2$SO$_2$NHEt | 3-I | 2,4-Cl$_2$ | |
| 1-262 | CHMeCH$_2$SO$_2$NHEt | 3-I | 2-Cl-4-Br | |
| 1-263 | CHMeCH$_2$SO$_2$NHEt | 3-I | 2-Cl-4-I | |
| 1-264 | CHMeCH$_2$SO$_2$NHEt | 3-I | 2,4-Br$_2$ | |
| 1-265 | CHMeCH$_2$SO$_2$NHEt | 3-I | 2-Br-4-I | |
| 1-266 | CHMeCH$_2$SO$_2$NHEt | 3-I | 2,3,4-Cl$_3$ | Amorphous |
| 1-267 | CHMeCH$_2$SO$_2$NEt$_2$ | 3-I | 2,3,4-Cl$_3$ | 114–118 |
| 1-268 | OMe$_2$CH$_2$SO$_2$NEt$_2$ | 3-I | 2,3,4-Cl$_3$ | 164–166 |
| 1-269 | CHMeCH$_2$SO$_2$NHEt | 3-I | 2,3-Cl$_2$-4-F | |
| 1-270 | CHMeCH$_2$SO$_2$NHEt | 3-I | 2,3-Cl$_2$-4-Br | |
| 1-271 | CHMeCH$_2$SO$_2$NHEt | 3-I | 2,3-Cl$_2$-4-I | |
| 1-272 | CHMeCH$_2$SO$_2$NHEt | 3-I | 2,4-Cl$_2$-3-Br | |
| 1-273 | CHMeCH$_2$SO$_2$NHEt | 3-I | 2,4-Cl$_2$-3-F | |
| 1-274 | CHMeCH$_2$SO$_2$NHEt | 3-I | 2-Me-4-OCHF$_2$ | |
| 1-275 | CHMeCH$_2$SO$_2$NHEt | 3-I | 2-Me-4-OCF$_3$ | 181–182 |
| 1-276 | CHMeCH$_2$SO$_2$NEt$_2$ | 3-I | 2-Me-4-OCF$_3$ | Amorphous |
| 1-277 | OMe$_2$CH$_2$SO$_2$NEt$_2$ | 3-I | 2-Me-4-OCF$_3$ | Amorphous |
| 1-278 | CHMeCH$_2$SO$_2$NHEt | 3-I | 2-Me-4-OCF$_2$CF$_3$ | |
| 1-279 | CHMeCH$_2$SO$_2$NHEt | 3-I | 2-Me-4-OCF$_2$CHF$_2$ | |
| 1-280 | CHMeCH$_2$SO$_2$NHEt | 3-I | 2-Me-4-OCF$_2$CHFCF$_3$ | |
| 1-281 | CHMeCH$_2$SO$_2$NHEt | 3-I | 2-Me-4-OCF$_2$CHFOCF$_3$ | |
| 1-282 | CHMeCH$_2$SO$_2$NHEt | 3-I | 2-Me-4-OCF$_2$CHFOC$_3$F$_7$-n | |
| 1-283 | CHMeCH$_2$SO$_2$NHEt | 3-I | 2-Cl-4-OCHF$_2$ | |
| 1-284 | CHMeCH$_2$SO$_2$NHEt | 3-I | 2-Cl-4-OCF$_3$ | |
| 1-285 | CHMeCH$_2$SO$_2$NEt$_2$ | 3-I | 2-Cl-4-OCF$_3$ | 100–103 |
| 1-286 | OMe$_2$CH$_2$SO$_2$NEt$_2$ | 3-I | 2-Cl-4-OCF$_3$ | 141–142 |
| 1-287 | CHMeCH$_2$SO$_2$NHEt | 3-I | 2-Cl-4-OCF2CF$_3$ | |
| 1-288 | CHMeCH$_2$SO$_2$NHEt | 3-I | 2-Cl-4-OCF$_2$CHF$_2$ | |
| 1-289 | CHMeCH$_2$SO$_2$NHEt | 3-I | 2-Cl-4-OCF$_2$CHFCF$_3$ | |
| 1-290 | CHMeCH$_2$SO$_2$NHEt | 3-I | 2-Cl-4-OCF$_2$CHFOCF$_3$ | |
| 1-291 | CHMeCH$_2$SO$_2$NHEt | 3-I | 2-Cl-4-OCF$_2$CHFOC$_3$F$_7$-n | |
| 1-292 | CHMeCH$_2$SO$_2$NHEt | 3-I | 2,3-Cl$_2$-4-OCF$_3$ | |
| 1-293 | CHMeCH$_2$SO$_2$NHEt | 3-I | 2,3-Cl$_2$-4-OCF$_2$CHF$_2$ | |
| 1-294 | CHMeCH$_2$SO$_2$NHEt | 3-I | 2,3-Cl$_2$-4-OCF$_2$CHFCF$_3$ | |
| 1-295 | CHMeCH$_2$SO$_2$NHEt | 3-I | 2,3-Cl$_2$-4-OCF$_2$CHFOCF$_3$ | |
| 1-296 | CHMeCH$_2$SO$_2$NHEt | 3-I | 2,3-Cl$_2$-4-OCF$_2$CHFOC$_3$F$_7$-n | |
| 1-297 | CHMeCH$_2$SO$_2$NHEt | 3-I | 4-CF$_2$CF$_2$CF$_3$ | |
| 1-298 | CHMeCH$_2$SO$_2$NHEt | 3-I | 4-CF(CF$_3$)$_2$ | |
| 1-299 | CHMeCH$_2$SO$_2$NHEt | 3-I | 2-Me-4-CF$_3$ | |
| 1-300 | CHMeCH$_2$SO$_2$NHEt | 3-I | 2-Me-4-CF$_2$CF$_3$ | |
| 1-301 | CHMeCH$_2$SO$_2$NEt$_2$ | 3-I | 2-Me-4-CF$_2$CF$_3$ | 118–120 |
| 1-302 | OMe$_2$CH$_2$SO$_2$NEt$_2$ | 3-I | 2-Me-4-CF$_2$CF$_3$ | Amorphous |
| 1-303 | OMe$_2$CH$_2$SO$_2$NHCH$_2$Ph | 3-I | 2-Me-4-CF$_2$CF$_3$ | 153–154 |
| 1-304 | OMe$_2$CH$_2$SO$_2$NHCH$_2$CH$_2$SMe | 3-I | 2-Me-4-CF$_2$CF$_3$ | 164–166 |
| 1-305 | OMe$_2$CH$_2$SO$_2$NHCH$_2$CH$_2$SOMe | 3-I | 2-Me-4-CF$_2$CF$_3$ | 150–152 |
| 1-306 | OMe$_2$CH$_2$SO$_2$NHCH$_2$CH$_2$SO$_2$Me | 3-I | 2-Me-4-CF$_2$CF$_3$ | 139–142 |
| 1-307 | OMe$_2$CH$_2$SO$_2$NHCH$_2$CH$_2$SEt | 3-I | 2-Me-4-CF$_2$CF$_3$ | 159–160 |
| 1-308 | OMe$_2$CH$_2$SO$_2$NHCH$_2$CH$_2$SOEt | 3-I | 2-Me-4-CF$_2$CF$_3$ | 198–199 |

TABLE 1-continued

General formula (I-1)

(I-1)

[Chemical structure diagram showing the general formula (I-1)]

| No. | —A—SO$_2$NR$^1$R$^2$ | Xm | Yn | Physical property: Melting point ° C. |
|---|---|---|---|---|
| 1-309 | OMe$_2$CH$_2$SO$_2$NHCH$_2$CH$_2$SO$_2$Et | 3-I | 2-Me-4-CF$_2$CF$_3$ | 133–134 |
| 1-310 | OMe$_2$CH$_2$SO$_2$NHCH$_2$CH$_2$SPh | 3-I | 2-Me-4-CF$_2$CF$_3$ | 144–145 |
| 1-311 | CHMeCH$_2$SO$_2$NHEt | 3-I | 2-Me-4-CF$_2$CF$_2$CF$_3$ | |
| 1-312 | CHMeCH$_2$SO$_2$NHEt | 3-I | 2-Cl-4-CF$_3$ | |
| 1-313 | CHMeCH$_2$SO$_2$NHEt | 3-I | 2-F-4-CF$_2$CF$_3$ | |
| 1-314 | CHMeCH$_2$SO$_2$NHEt | 3-I | 2-Cl-4-CF$_2$CF$_3$ | |
| 1-315 | CHMeCH$_2$SO$_2$NHEt | 3-I | 2-Cl-4-CF$_2$CF$_2$CF$_3$ | |
| 1-316 | CHMeCH$_2$SO$_2$NHEt | 3-I | 2-F-4-CF(CF$_3$)$_2$ | |
| 1-317 | CHMeCH$_2$SO$_2$NHEt | 3-I | 2-Cl-4-CF(CF$_3$)$_2$ | |
| 1-318 | CHMeCH$_2$SO$_2$NHEt | 3-I | 2-Br-4-CF(CF$_3$)$_2$ | |
| 1-319 | CHMeCH$_2$SO$_2$NHEt | 3-I | 2-I-4-CF(CF$_3$)$_2$ | |
| 1-320 | CHMeCH$_2$SO$_2$NHEt | 3-I | 2-Et-4-CF(CF$_3$)$_2$ | |
| 1-321 | CHMeCH$_2$SO$_2$NHEt | 3-I | 2-n-Pr-4-CF(CF$_3$)$_2$ | |
| 1-322 | CHMeCH$_2$SO$_2$NHEt | 3-I | 2-i-Pr-4-CF(CF$_3$)$_2$ | |
| 1-323 | CHMeCH$_2$SO$_2$NHEt | 3-I | 2-t-Bu-4-CF(CF$_3$)$_2$ | |
| 1-324 | CHMeCH$_2$SO$_2$NHEt | 3-I | 2-Ph-4-CF(CF$_3$)$_2$ | |
| 1-325 | CHMeCH$_2$SO$_2$NHEt | 3-I | 2-CH$_2$OH-4-CF(CF$_3$)$_2$ | |
| 1-326 | CHMeCH$_2$SO$_2$NHEt | 3-I | 2-CH$_2$OMe-4-CF(CF$_3$)$_2$ | |
| 1-327 | CHMeCH$_2$SO$_2$NHEt | 3-I | 2-OMe-4-CF(CF$_3$)$_2$ | |
| 1-328 | CHMeCH$_2$SO$_2$NHEt | 3-I | 2-SMe-4-CF(CF$_3$)$_2$ | |
| 1-329 | CHMeCH$_2$SO$_2$NHEt | 3-I | 2-N(Me)$_2$-4-CF(CF$_3$)$_2$ | |
| 1-330 | CHMeCH$_2$SO$_2$NHEt | 3-I | 2-NO$_2$-4-CF(CF$_3$)$_2$ | |
| 1-331 | CHMeCH$_2$SO$_2$NHEt | 3-I | 2-CF$_3$-4-CF(CF$_3$)$_2$ | |
| 1-332 | CHMeCH$_2$SO$_2$NHEt | 3-I | 2-CHO-4-CF(CF$_3$)$_2$ | |
| 1-333 | CHMeCH$_2$SO$_2$NHEt | 3-I | 2-CN-4-CF(CF$_3$)$_2$ | |
| 1-334 | CHMeCH$_2$SO$_2$NHEt | 3-I | 2-COMe-4-CF(CF$_3$)$_2$ | |
| 1-335 | CHMeCH$_2$SO$_2$NHEt | 3-I | 2,3-(Me)$_2$-4-CF(CF$_3$)$_2$ | |
| 1-336 | CHMeCH$_2$SO$_2$NHEt | 3-I | 2-Me-3-F-4-CF(CF$_3$)$_2$ | |
| 1-337 | CHMeCH$_2$SO$_2$NHEt | 3-I | 2-Me-3-Cl-4-CF(CF$_3$)$_2$ | |
| 1-338 | CHMeCH$_2$SO$_2$NHEt | 3-I | 2-Me-3-OH-4-CF(CF$_3$)$_2$ | |
| 1-339 | CHMeCH$_2$SO$_2$NHEt | 3-I | 2-Me-3-OMe-4-CF(CF$_3$)$_2$ | |
| 1-340 | CHMeCH$_2$SO$_2$NHEt | 3-I | 2-Me-5-F-4-CF(CF$_3$)$_2$ | |
| 1-341 | CHMeCH$_2$SO$_2$NHEt | 3-I | 2-Me-5-Cl-4-CF(CF$_3$)$_2$ | |
| 1-342 | CHMeCH$_2$SO$_2$NH$_2$ | 3-I | 2-Me-4-CH(CF$_3$)$_2$ | 214–216 |
| 1-343 | CHMeCH$_2$SO$_2$NHEt | 3-I | 2-Me-4-CH(CF$_3$)$_2$ | 232–234 |
| 1-344 | OMe$_2$CH$_2$SO$_2$NEt$_2$ | 3-I | 2-Me-4-CH(CF$_3$)$_2$ | Amorphous |
| 1-345 | OMe$_2$CH$_2$SO$_2$N(CH$_2$)$_4$ | 3-I | 2-Me-4-CH(CF$_3$)$_2$ | Amorphous |
| 1-346 | CHMeCH$_2$SO$_2$NHEt | 3-I | 2-Me-4-C(OH)(CF$_3$)$_2$ | |
| 1-347 | CHMeCH$_2$SO$_2$NHEt | 3-I | 2-Me-4-C(OMe)(CF$_3$)$_2$ | |
| 1-343 | CHMeCH$_2$SO$_2$NHEt | 3-I | 2-Me-4-C(OEt)(CF$_3$)$_2$ | |
| 1-349 | CHMeCH$_2$SO$_2$NHEt | 3-I | 2-OCF$_2$O-3-4-CF(CF$_3$)$_2$ | |
| 1-350 | CHMeCH$_2$SO$_2$NHEt | 3-I | 2-OCH$_2$O-3-4-CF(CF$_3$)$_2$ | |
| 1-351 | CHMeCH$_2$SO$_2$NHEt | 3-I | 2-(CH$_2$)$_3$-3-4-CF(CF$_3$)$_2$ | |
| 1-352 | CHMeCH$_2$SO$_2$NHEt | 3-I | 2-(CH$_2$)$_4$-3-4-CF(CF$_3$)$_2$ | |
| 1-353 | CHMeCH$_2$SO$_2$NHEt | 3-I | 2-Me-4-CF(CF$_3$)CF$_2$CF$_3$ | |

TABLE 2

General formula (I-2)

(I-2)

[Chemical structure of general formula I-2 with substituents $X_m$, $Y_n$, $R^1$, $R^2$, A, $SO_2$, NH groups on a phthalamide core]

| No. | —A—SO$_2$NR$^1$R$^2$ | Xm | Yn | Physical property: Melting point ° C. |
|---|---|---|---|---|
| 2-1 | CHMeCH$_2$SO$_2$NHEt | 3-I | 4-CF(CF$_3$)$_2$ | |
| 2-2 | CHMeCH$_2$SO$_2$NH$_2$ | 3-I | 2-Me-4-CF(CF$_3$)$_2$ | |
| 2-3 | CHMeCH$_2$SO$_2$NHMe | 3-I | 2-Me-4-CF(CF$_3$)$_2$ | |
| 2-4 | CHMeCH$_2$SO$_2$NMe$_2$ | 3-I | 2-Me-4-CF(CF$_3$)$_2$ | |
| 2-5 | CHMeCH$_2$SO$_2$NHEt | 3-I | 2-Me-4-CF(CF$_3$)$_2$ | Amorphous |
| 2-6 | CHMeCH$_2$SO$_2$NEt$_2$ | 3-I | 2-Me-4-CF(CF$_3$)$_2$ | |
| 2-7 | CMe$_2$CH$_2$SO$_2$NEt$_2$ | 3-I | 2-Me-4-CF(CF$_3$)$_2$ | Amorphous |
| 2-8 | CHMeCH$_2$SO$_2$NHEt | 3-I | 2-Cl-4-CF(CF$_3$)$_2$ | |
| 2-9 | CHMeCH$_2$SO$_2$NHEt | 3-I | 2-OMe-4-CF(CF$_3$)$_2$ | |
| 2-10 | CHMeCH$_2$SO$_2$NHEt | 3-I | 2-SMe-4-CF(CF$_3$)$_2$ | |
| 2-11 | CHMeCH$_2$SO$_2$NHEt | 3-I | 2-SOMe-4-CF(CF$_3$)$_2$ | |
| 2-12 | CHMeCH$_2$SO$_2$NHEt | 3-I | 2-SO$_2$Me-4-CF(CF$_3$)$_2$ | |
| 2-13 | CHMeCH$_2$SO$_2$NHEt | 3-I | 2-Et-4-CF(CF$_3$)$_2$ | |
| 2-14 | CHMeCH$_2$SO$_2$NHEt | 3-I | 2-n-Pr-4-CF(CF$_3$)$_2$ | |
| 2-15 | CHMeCH$_2$SO$_2$NHEt | 3-I | 4-CH(CF$_3$)$_2$ | |
| 2-16 | CHMeCH$_2$SO$_2$NHEt | 3-I | 2-Me-4-CH(CF$_3$)$_2$ | Amorphous |
| 2-17 | CHMeCH$_2$SO$_2$NHEt | 3-I | 2-Cl-4-CH(CF$_3$)$_2$ | |
| 2-18 | CHMeCH$_2$SO$_2$NHEt | 3-I | 2-OMe-4-CH(CF$_3$)$_2$ | |
| 2-19 | CHMeCH$_2$SO$_2$NHEt | 3-I | 2-SMe-4-CH(CF$_3$)$_2$ | |
| 2-20 | CHMeCH$_2$SO$_2$NHEt | 3-I | 2-SOMe-4-CH(CF$_3$)$_2$ | |
| 2-21 | CHMeCH$_2$SO$_2$NHEt | 3-I | 2-SO$_2$Me-4-CH(CF$_3$)$_2$ | |
| 2-22 | CHMeCH$_2$SO$_2$NHEt | 3-I | 2-Et-4-CH(CF$_3$)$_2$ | |
| 2-23 | CHMeCH$_2$SO$_2$NHEt | 3-I | 2-n-Pr-4-CH(CF$_3$)$_2$ | |

Table 3 shows $^1$H-NMR data of compounds having a physical property expressed by the word "amorphous" in Table 1 and Table 2.

TABLE 3

| No. | NMR data $^1$H-NMR[CDCl$_3$ (or DMSO-d$_6$)/TMS, δvalues (ppm)] |
|---|---|
| 1-62 (CDCl$_3$) | 1.30(d, 3H), 1.60(s, 6H), 2.38(s, 3H), 2.80(m, 2H), 3.30(m, 3H), 3.43(s, 2H), 4.00(m, 1H), 4.50(m, 1H), 6.45(br, 1H), 7.25(m, 1H), 7.48(m, 2H), 7.76(d, 1H), 7.98(d, 1H), 8.29(d, 1H), 8.40(br, 1H) |
| 1-147 (CDCl$_3$) | 1.09(d, 3H), 1.44(d, 3H), 2.05(s, 3H), 2.37(s, 3H), 2.43(m, 2H), 3.32(m, 2H), 3.63(m, 1H), 4.63(m, 1H), 5.46(br, 1H), 6.70(br, 1H), 7.21(t, 1H), 7.36(d, 1H), 7.44(s, 1H), 7.70(d, 1H), 7.90(m, 2H), 8.64(br, 1H) |
| 1-149 (CDCl$_3$) | 1.19(d, 3H), 1.37(d, 3H), 2.33(s, 3H), 2.83(s, 3H), 3.52(m, 2H), 3.27(d, 2H), 3.98(m, 1H), 4.55(m, 1H), 5.98(br, 1H), 6.88(br, 1H), 7.11(t, 1H), 7.33(d, 1H), 7.42(s, 1H), 7.60(m, 1H), 7.83(m, 2H), 8.89(br, 1H) |
| 1-175 (DMSO-d$_6$) | 1.49(s, 6H), 2.35(s, 3H), 3.65(s, 2H), 6.91(br, 2H), 7.25(m, 1H), 7.51(d, 1H), 7.52(s, 1H), 7.70(d, 1H), 7.78(d, 1H), 7.99(d, 1H), 8.29(s, 1H), 9.87(br, 1H) |
| 1-176 (CDCl$_3$) | 1.63(s, 6H), 2.39(s, 3H), 2.56(s, 3H), 3.41(s, 2H), 4.21(br, 1H), 6.48(br, 1H), 7.20(m, 1H), 7.47(m, 2H), 7.74(d, 1H), 7.99(d, 1H), 8.30(br, 1H), 8.32(d, 1H) |
| 1-178 (CDCl$_3$) | 1.01(t, 3H), 1.61(s, 6H), 2.38(s, 3H), 2.98(q, 2H), 3.40(s, 2H), 4.52(br, 1H), 6.63(br, 1H), 7.19(m, 1H), 7.43(m, 2H), 7.71(d, 1H), 7.95(d, 1H), 8.21(d, 1H), 8.46(br, 1H) |
| 1-179 (CDCl$_3$) | 1.08(t, 6H), 1.61(s, 6H), 2.34(s, 3H), 3.12(q, 4H), 3.21(s, 2H), 6.75(br, 1H), 7.20(m, 1H), 7.43(m, 2H), 7.75(d, 1H), 7.96(d, 1H), 8.37(d, 1H), 8.50(br, 1H) |
| 1-266 (DMSO-d$_6$) | 1.00(t, 3H), 1.28(d, 3H), 2.84(m, 4H), 4.27(m, 1H), 7.14(br, 1H), 7.28(m, 1H), 7.67(m, 3H), 8.03(d, 1H), 8.52(d, 1H), 10.14(br, 1H) |
| 1-276 (CDCl$_3$) | 1.10(t, 6H), 1.46(d, 3H), 2.31(s, 3H), 3.15(m, 5H), 3.67(m, 1H), 4.60(m, 1H), 6.80(br, 1H), 7.04(s, 1H), 7.21(t, 1H), 7.25(d, 1H), 7.74(d, 1H), 7.95(d, 1H), 8.01(d, 1H), 8.26(br, 1H) |
| 1-277 (CDCl$_3$) | 1.11(t, 6H), 1.63(s, 6H), 2.33(s, 3H), 3.14(q, 4H), 3.20(s, 2H), 6.67(br, 1H), 7.12(d, 1H), 7.21(m, 2H), 7.77(d, 1H), 7.97(d, 1H), 8.18(d, 1H), 8.30(br, 1H) |
| 1-302 (CDCl$_3$) | 1.10(t, 6H), 1.62(s, 6H), 2.38(s, 3H), 3.12(q, 4H), 3.16(s, 2H), 6.68(br, 1H), 7.22(m, 1H), 7.43(m, 2H), 7.79(d, 1H), 7.99(d, 1H), 8.43(br, 1H), 8.45(d, 1H) |
| 1-344 (CDCl$_3$) | 1.09(t, 6H), 1.62(s, 6H), 2.35(s, 3H), 3.13(q, 4H), 3.20(s, 2H), 3.99(m, 1H), 6.63(br, 1H), 7.26(m, 3H), 7.78(d, 1H), 7.98(d, 1H), 8.33(d, 1H), 8.35(br, 1H) |
| 1-345 (CDCl$_3$) | 1.63(s, 6H), 1.78(m, 4H), 2.35(s, 3H), 3.19(m, 4H), 3.26(s, 2H), 3.99(m, 1H), 6.68(br, 1H), 7.23(m, 3H), 7.77(d, 1H), 7.98(d, 1H), 8.31(d, 1H), 8.33(br, 1H) |
| 2-5 (CDCl$_3$) | 1.05(t, 3H), 1.47(d, 3H), 2.59(s, 3H), 3.05(m, 2H), 3.25(d, 2H), 4.50(m, 1H), 5.05(br, 1H), 6.65(br, 1H), 7.25(m, 1H), 7.45(d, 1H), 7.73(d, 1H), 7.97(d, 1H), 8.33(d, 1H), 8.63(br, 1H) |
| 2-7 (CDCl$_3$) | 1.08(t, 6H), 1.63(s, 6H), 2.62(s, 38), 3.12(q, 4H), 3.18(s, 2H), 6.79(br, 1H), 7.22(m, 1H), 7.53(d, 1H), 7.77(d, 1H), 7.98(d, 1H), 8.73(d, 1H), 8.78(br, 1H) |
| 2-16 (CDCl$_3$) | 1.01(t, 3H), 1.46(d, 3H), 2.55(s, 3H), 3.03(m, 2H), 3.24(d, 2H), 4.40(m, 2H), 5.10(br, 1H), 6.65(br, 1H), 7.25(m, 2H), 7.71(d, 1H), 7.93(d, 1H), 8.14(d, 1H), 8.74(br, 1H) |

EXAMPLES

Typical examples of the present invention are described below but they should not be construed as limiting the scope of the invention.

Example 1

Production of N$^2$-(2-ethylsulfamoyl-1-methylethyl)-3-iodo-N$^1$-{2-methyl-4-[1,2,2,2-tetrafluoro-1-(trifluoromethyl)ethyl]phenyl}phthalamide (compound No. 1–4)

(1-1) In tetrahydrofuran (500 ml) was dissolved 22.53 g (300 mmol) of 2-aminopropanol, and then 155.1 g (300 mmol) of a 30% solution of carbobenzoxy chloride in toluene and a solution of 36.43 g (360 mmol) of triethylamine in tetrahydrofuran were slowly dropped thereinto under ice-cooling. After the resulting mixture was stirred at room temperature for 3 hours, the triethylamine hydrochloride precipitated was filtered under reduced pressure and washed with ethyl acetate. The filtrate was concentrated under reduced pressure and diluted hydrochloric acid was added thereto, followed by three runs of extraction with ethyl acetate. The organic layer was washed with saturated aqueous sodium hydrogencarbonate solution and then saturated aqueous sodium chloride solution, dried over anhydrous sodium sulfate, and then distilled to remove the solvent, whereby 49.8 g (yield 79%) of benzyl (2-hydroxy-1-methylethyl)carbamate was obtained.

(1-2) In tetrahydrofuran (400 ml) were dissolved 46.5 g (222 mmol) of benzyl (2-hydroxy-1-methylethyl)carbamate and 26.96 g (266 mmol) of triethylamine, and a solution of 27.96 g (244 mmol) of methanesulfonyl chloride in tetrahydrofuran was slowly dropped thereinto at 0° C. After the resulting mixture was stirred at room temperature for 5 hours, the triethylamine hydrochloride precipitated was filtered under reduced pressure and washed with ethyl acetate. The filtrate was concentrated under reduced pressure and water was added thereto, followed by three runs of extraction with ethyl acetate. The extract solution was washed with saturated aqueous sodium hydrogencarbonate solution and then saturated aqueous sodium chloride solution, and dried over anhydrous sodium sulfate. The solvent was distilled off and the crude crystals thus obtained were washed twice with a solvent (hexane:ethyl acetate=4:1) to obtain 49.5 g (yield 78%) of 2-(benzyloxycarbonylamino)propyl methanesulfonate.

(1-3) In ethanol (120 ml) was dissolved 34.9 g (120 mmol) of 2-(benzyloxycarbonylamino)propyl methanesulfonate, followed by adding dropwise thereto a thiolate separately prepared from 14.42 g (120 mmol) of thioglycolic acid and a solution of sodium ethoxide (120 mmol) in ethanol. The reaction was carried out at room temperature for 30 minutes and then at 50° C. for 2 hours, after which the solvent was distilled off and water was added to the residue, followed by three runs of extraction with ethyl acetate. The extract solution was washed with saturated aqueous sodium hydrogencarbonate solution and then saturated aqueous sodium chloride solution, and dried over anhydrous sodium sulfate. The solvent was distilled off and the resulting residue was purified by silica gel column chromatography (hexane:ethyl acetate=4:1) to obtain 34.5 g (yield 92%) of 2-(benzyloxycarbonylamino)propylthioacetic acid.

(1-4) In ethyl acetate (150 ml) was dissolved 34.5 g (110 mmol) of 2-(benzyloxycarbonylamino)propylthioacetic acid, and a solution (50 ml) of 23.9 g (110 mmol) of m-chloroperbenzoic acid in ethyl acetate was slowly dropped thereinto at 0° C. After the reaction was carried out at room temperature for 3 hours, the reaction solution was poured into saturated aqueous sodium hydrogencarbonate solution, followed by extraction with ethyl acetate. The extract solution was washed three times with saturated aqueous sodium hydrogencarbonate solution and then once with saturated aqueous sodium chloride solution, and dried over anhydrous sodium sulfate. The solvent was distilled off and the crude crystals thus obtained were washed twice with a solvent (hexane:ethyl acetate=2:1) to obtain 30.38 g (yield 84%) of 2-(benzyloxycarbonylamino)propylsulfinylacetic acid.

(1-5) In methanol (300 ml) was suspended 30.38 g (93 mmol) of 2-(benzyloxycarbonylamino)propylsulfinylacetic acid, followed by adding thereto 19.04 g (75 mmol) of iodine, and the reaction was carried out with refluxing for 5 hours. An aqueous sodium hydrogensulfite solution was added to the reaction mixture to reduce the excess iodine, after which the solution thus obtained was made weakly basic with saturated aqueous sodium hydrogencarbonate solution and sodium hydrogencarbonate and the methanol was distilled off. Water was added to the residue, followed by three runs of extraction with ethyl acetate. The extract solution was washed with saturated aqueous sodium chloride solution and dried over anhydrous sodium sulfate.

The solvent was distilled off and the thus obtained crude bis[2-(benzyloxycarbonylamino)propyl]-disulfide (29 mmol, estimated from $^1$H-NMR integral ratio) was suspended in ethanol (150 ml), followed by adding thereto 15.66 g (88 mmol) of N-bromosuccinimide in small portions. The reaction was carried out at room temperature for 3 hours, after which the reaction solution was made weakly basic with saturated aqueous sodium hydrogencarbonate solution and sodium hydrogencarbonate and the ethanol was distilled off. Water was added to the residue, followed by three runs of extraction with ethyl acetate. The extract solution was washed three times with water and then once with saturated aqueous sodium chloride solution and dried over anhydrous sodium sulfate. The solvent was distilled off and the resulting residue was purified by silica gel column chromatography (hexane:ethyl acetate=2:1) to obtain 16.0 g (yield 60%) of ethyl 2-(benzyloxycarbonylamino)propane-1-sulfinate.

(1-6) In ethanol (7 ml) was dissolved 2.2 g (7.4 mmol) of ethyl 2-(benzyloxycarbonylamino)propane-1-sulfinate, and 3.2 g (8 mmol) of 10% aqueous sodium hydroxide solution was slowly dropped thereinto under ice-cooling. The reaction was carried out at room temperature for 1 hour, after which the ethanol was distilled off and water was added to the residue, followed by two runs of extraction with methyl t-butyl ether. The aqueous layer was acidified with concentrated hydrochloric acid, followed by three runs of extraction with ethyl acetate. The extract solution was washed with saturated aqueous sodium chloride solution and dried over anhydrous sodium sulfate. The solvent was distilled off and the crude crystals thus obtained were washed twice with a solvent (hexane:ethyl acetate=4:1) to obtain 1.73 g (yield 91%) of 2-(benzyloxycarbonylamino)propane-1-sulfinic acid.

(1-7) In water (10 ml) was dissolved 0.52 g (3.8 mmol) of potassium carbonate and 1.73 g (6.7 mmol) of 2-(benzyloxycarbonylamino)propane-1-sulfinic acid was added thereto, after which 1.07 g (6.7 mmol) of bromine was added dropwise thereto (water was properly added because crystals were precipitated during the dropwise addition to make stirring difficult). After stirring at room temperature for 30 minutes, the crystals were filtered and then washed with water to obtain 2.30 g (quantitative) of 2-(benzyloxycarbonylamino)propane-1-sulfonyl bromide.

(1-8) A solution (5 ml) of 1.44 g (3.3 mmol) of 2-(benzyloxycarbonylamino)propane-1-sulfonyl bromide in tetrahydrofuran was added dropwise to 70% aqueous ethylamine solution (10 ml) under ice-cooling. The reaction was carried out at room temperature for 1 hour, after which the reaction mixture was poured into diluted hydrochloric acid, followed by three runs of extraction with ethyl acetate. The extract solution was washed with saturated aqueous sodium chloride solution and dried over anhydrous sodium sulfate. The solvent was distilled off to obtain crude N-ethyl-2-(benzyloxycarbonylamino)propane-1-sulfonamide, and this crude product was used without further purification in the subsequent reaction.

(1-9) In a bottle for pressure hydrogenation, the inner atmosphere of which had been replaced with argon, was placed 0.07 g of 10% Pd—C, and suspended by adding ethanol (10 ml) thereto all at once. Then, a solution (20 ml) of the crude N-ethyl-2-(benzyloxycarbonylamino)propane-1-sulfonamide obtained in (1-8) in ethanol was added thereto and the reaction was carried out for 10 hours under pressure (hydrogen pressure: 4 kg/cm$^2$) (during the reaction, the pressure was reduced for reducing the partial pressure of carbon monoxide produced, and then was re-increased). The reaction solution was filtered with Celite and washed with ethanol, and the filtrate was concentrated under reduced pressure. The crystals thus obtained were washed twice with a solvent (hexane:ethyl acetate=2:1) to obtain 0.27 g {yield from 2-(benzyloxycarbonylamino)propane-1-sulfonyl bromide: 50%} of N-ethyl-2-aminopropane-1-sulfonamide.

(1-10) In acetonitrile (100 ml) was dissolved 5.5 g (20 mmol) of 3-iodophthalic anhydride, and a solution (20 ml) of 5.5 g (20 mmol) of 2-methyl-4-[1,2,2,2-tetrafluoro-1-(trifluoromethyl)ethyl]aniline in acetonitrile was slowly dropped thereinto. After the resulting mixture was stirred at room temperature for 3 hours, two-thirds of the acetonitrile was distilled off under reduced pressure and the crystals precipitated were filtered and then washed with acetonitrile to obtain 5.6 g (yield 51%) of 6-iodo-N-{2-methyl-4-[1,2,2,2-tetrafluoro-1-(trifluoromethyl)ethyl]phenyl}phthalamic acid.

(1-11) In methyl t-butyl ether (60 ml) was suspended 5.47 g (10 mmol) of 6-iodo-N-{2-methyl-4-[1,2,2,2-tetrafluoro-1-(trifluoromethyl)ethyl]phenyl}phthalamic acid, and a solution of 3.15 g (15 mmol) of trifluoroacetic anhydride in methyl t-butyl ether was slowly dropped thereinto. The resulting mixture was stirred at room temperature for 3 hours and then poured into ice water, followed by three runs of extraction with ethyl acetate. The extract solution was washed twice with saturated aqueous sodium hydrogencarbonate solution and then once with saturated aqueous sodium chloride solution, and dried over anhydrous sodium sulfate. The solvent was distilled off and the crude crystals thus obtained were washed twice with a solvent (hexane:ethyl acetate=4:1) to obtain 5.0 g (yield 94%) of 1,3-dihydro-7-iodo-3-{2-methyl-4-[1,2,2,2-tetrafluoro-1-(trifluoro-methyl)ethyl]phenylimino}-2-benzofuran-1-one.

(1-12) In acetonitrile (10 ml) was dissolved 0.42 g (0.8 mmol) of 1,3-dihydro-7-iodo-3-{2-methyl-4-[1,2,2,2-tetrafluoro-1-(trifluoromethyl)ethyl]phenylimino}-2-benzofuran-1-one, followed by adding thereto 0.13 g (0.8 mmol) of the N-ethyl-2-aminopropane-1-sulfonamide obtained in (1-9), and the reaction was carried out at room temperature for 10 hours. The solvent was distilled off and the crystals precipitated were filtered, and washed with acetonitrile and then with a mixed solvent (hexane:ethyl acetate=4:1) to obtain 0.45 g (yield 81%) of $N^2$-(2-ethylsulfamoyl-1-methylethyl)-3-iodo-$N^1$-{2-methyl-4-[1,2,2,2-tetrafluoro-1-(trifluoromethyl)ethyl]phenyl}phthalamide.

Melting point: 170–172° C.

Example 2

Production of 3-iodo-$N^1$-{2-methyl-4-[1,2,2,2-tetrafluoro-1-(trifluoromethyl)ethyl]phenyl}-$N^2$-(2-sulfamoyl-1,1-dimethylethyl)phthalamide (compound No. 1–175)

(2-1) In tetrahydrofuran (300 ml) was dissolved 23.86 g (200 mmol) of 1,1-dimethyl-2-(methylthio)ethylamine, and 103.4 g (200 mmol) of a 30% solution of carbobenzoxy chloride in toluene and then a solution of 24.29 g (240 mmol) of triethylamine in tetrahydrofuran were slowly dropped thereinto under ice-cooling. After the resulting mixture was stirred at room temperature for 3 hours, the triethylamine hydrochloride precipitated was filtered under reduced pressure and washed with ethyl acetate. The filtrate was concentrated under reduced pressure and the residue was purified by silica gel column chromatography (hexane:ethyl acetate=4:1) to obtain 36.35 g (yield 72%) of benzyl 1,1-dimethyl-2-(methylthio)ethylcarbamate.

(2-2) To a solution of 45.4 g (179 mmol) of benzyl 1,1-dimethyl-2-(methylthio)ethylcarbamate in aqueous methanol (obtained by adding 5.22 g (290 mmol) of water to 150 ml of methanol) was added 33.46 g (188 mmol) of N-bromosuccinimide in small portions with stirring. The reaction was carried out at room temperature for 2 hours, after which the reaction solution was made weakly basic with saturated aqueous sodium hydrogencarbonate solution and then the methanol was distilled off. Water was added to the residue, followed by three runs of extraction with ethyl acetate. The extract solution was washed three times with water and then once with saturated aqueous sodium chloride solution, and dried over anhydrous sodium sulfate. The solvent was distilled off and the thus obtained crude benzyl 1,1-dimethyl-2-(methylsulfinyl)ethylcarbamate was dissolved in acetic anhydride (150 ml), and the reaction was carried out with refluxing for 4 hours. The excess acetic anhydride and acetic acid were distilled off under reduced pressure to obtain a residue containing crude [2-(benzyloxycarbonylamino)-2-methylpropyl]thiomethyl acetate. This residue was dissolved in methanol (300 ml), followed by adding thereto 19.54 g (77 mmol) of iodine, and the reaction was carried out with refluxing for 5 hours. After the reaction mixture was cooled to room temperature, an aqueous sodium hydrogensulfite solution was added thereto to reduce the excess iodine. The reaction solution was made weakly basic with saturated aqueous sodium hydrogencarbonate solution, after which the methanol was distilled off. Water was added to the residue, followed by three runs of extraction with ethyl acetate. The extract solution was washed with saturated aqueous sodium chloride solution and dried over anhydrous sodium sulfate. The solvent was distilled off and the resulting residue was purified by silica gel column chromatography (hexane:ethyl acetate=4:1) to obtain 10.0 g (yield 23%) of bis[2-(benzyloxycarbonylamino)-2-methylpropyl]-disulfide.

(2-3) In ethanol (150 ml) was dissolved 10.0 g (21 mmol) of bis[2-(benzyloxycarbonylamino)-2-methylpropyl]disulfide, and 11.21 g (63 mmol) of N-bromosuccinimide was added thereto in small portions with stirring. The reaction was carried out at room temperature for 2 hours, after which the reaction solution was made weakly basic with saturated aqueous sodium hydrogencarbonate solution and the ethanol was distilled off. Water was added to the residue, followed by three runs of extraction with ethyl acetate. The extract solution was washed three times with water and then once with saturated aqueous sodium chloride solution and dried over anhydrous sodium sulfate. The solvent was distilled off and the resulting residue was purified by silica gel column chromatography (hexane:ethyl acetate=2:1) to obtain 10.45 g (yield 83%) of ethyl 2-(benzyloxycarbonylamino)-2-methypropane-1-sulfinate.

(2-4) In ethanol (10 ml) was dissolved 0.60 g (2 mmol) of ethyl 2-(benzyloxycarbonylamino)-2-methylpropane-1-sulfinate, and 0.9 g (2.2 mmol) of 10% aqueous sodium hydroxide solution was slowly dropped thereinto under ice-cooling. The reaction was carried out at room temperature for 1 hour and then the ethanol was distilled off. Water (10 ml), 0.18 g (2.2 mmol) of sodium acetate and 0.25 g (2.2 mmol) of hydroxylamine-O-sulfonic acid were added to the residue, and the reaction was carried out at room temperature for 1 hour. The reaction mixture was poured into water, followed by three runs of extraction with ethyl acetate. The extract solution was washed with saturated aqueous sodium hydrogencarbonate solution and then saturated aqueous sodium chloride solution, and dried over anhydrous sodium sulfate. The solvent was distilled off and 0.49 g (yield 86%) of the thus obtained crude 2-(benzyloxycarbonylamino)-2-methylpropane-1-sulfonamide was used without further purification in the subsequent reaction.

(2-5) In a bottle for pressure hydrogenation, the inner atmosphere of which had been replaced with argon, was placed 0.20 g of 10% Pd—C, and suspended by adding acetic acid (5 ml) thereto all at once. Then, a solution (10 ml) of the 2-(benzyloxycarbonylamino)-2-methylpropane-1-sulfonamide obtained in (2-4) in acetic acid was added thereto and the reaction was carried out for 10 hours under pressure (hydrogen pressure: 4 kg/cm$^2$) (during the reaction, the pressure was reduced for reducing the partial pressure of carbon monoxide produced, and then was re-increased). The reaction solution was filtered with Celite and washed with ethanol, after which the filtrate was concentrated under reduced pressure and the residue (crude 2-amino-2-methylpropane-1-sulfonamide acetate) was used without further purification in the subsequent reaction.

(2-6) In acetonitrile (10 ml) was dissolved 0.8 g (1.5 mmol) of 1,3-dihydro-7-iodo-3-{2-methyl-4-[1,2,2,2-tetrafluoro-1-(trifluoromethyl)ethyl]phenylimino}-2-benzofuran-1-one, followed by adding thereto the crude 2-amino-2-methylpropane-1-sulfonamide acetate obtained in (2-5) and 0.17 g (1.7 mmol) of triethylamine, and the reaction was carried out at room temperature for 30 hours. The solvent was distilled off and the resulting residue was purified by silica gel column chromatography (hexane:ethyl acetate=1:1) to obtain 0.05 g (yield 9%) of 3-iodo-N$^1$-{2-methyl-4-[1,2,2,2-tetrafluoro-1-(trifluoromethyl)ethyl]phenyl}-N$^2$-(2-sulfamoyl-1,1-dimethylethyl)phthalamide as an amorphous substance.

$^1$H-NMR [DMSO-d$_6$/TMS, 5 values (ppm)] 1.49(s, 6H), 2.35(s, 3H), 3.65(s, 2H), 6.91(br, 2H), 7.25(m, 1H), 7.51(d, 1H), 7.52(s, 1H), 7.70(d, 1H), 7.78(d, 1H), 7.99(d, 1H), 8.29(s, 1H), 9.87(br, 1H).

The agrohorticultural insecticides containing the sulfonamide derivative of general formula (I) or salt thereof of the present invention as an active ingredient are suitable for controlling various insect pests such as agrohorticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophyes orana fasciata*), smaller tea tortrix (*Adoxophyes sp.*), Manchurian fruit moth (*Grapholita inopinata*), oriental fruit moth (*Grapholita molesta*), soybean pod border (*Leguminivora glycinivorella*), mulberry leafroller (*Olethreutes mori*), tea leafroller (*Caloptilia thevivora*), *Caloptilia sp.* (*Caloptilia zachrysa*), apple leafminer (*Phyllonorycter ringoniella*), pear barkminer (*Spulerrina astaurota*), common white (*Piers rapae crucivora*), tobacco budworm (*Heliothis sp.*), codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolobus taonabae*), sweetpotato whitefly (*Bemisia tabaci*), greenhouse whitefly (*Trialeurodes vaporariorum*), turnup aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unaspis yanonensis*), etc.; TYLENCHIDA including soybean beetle (*Anomala rufocuprea*), Japanese beetle (*Popillia japonica*), tobacco beetle (*Lasioderma sericorne*), powderpost beetle (*Lyctus brunneus*), twenty-eight-spotted ladybird (*Epilachna vigintiotopunctata*), azuki bean weevil (*Callosobruchus chinensis*), vegetable weevil (*Listroderes costirostris*), maize weevil (*Sitophilus zeamais*), boll weevil (*Anthonomus grandis grandis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica sp.*), etc.; DIPTERA including melon fly (*Dacus(Zeugodacus) cucurbitae*), oriental fruit fly (*Dacus(Bactrocera) dorsalis*), rice leafminer (*Agromyza oryzae*), onion maggot (*Delia antiqua*), seedcorn maggot (*Delia platura*), soybean pod gall midge (*Asphondylia sp.*), muscid fly (*Musca domestica*), house mosquito (*Culex pipiens pipiens*), etc.; TYLENCHIDA including root-lesion nematode (*Pratylenchus sp.*), coffee root-lesion nematode (*Pratylenchus coffeae*), potato cyst nematode (*Globodera rostochiensis*), root-knot nematode (*Meloidogyne sp.*), citrus nematode (*Tylenchulus semipenetrans*), *Aphelenchus sp.* (*Aphelenchus avenae*), chrysanthemum foliar (*Aphelenchoides ritzemabosi*), etc.; and ACARINA including citrus red mite (*Panonychus citri*), European red mite (*Panonychus ulmi*), carmine spider mite (*Tetranychus cinnabarinus*), Kanzawa spider mite (*Tetranychus kanzawai Kishida*), two-spotted spider mite (*Tetranychus urticae Koch*), pink tea rust mite (*Acaphylla theae*), pink citrus rust mite (*Aculops pelekassi*), purple tea mite (*Calacarus carinatus*), pear rust mite (*Epitrimerus pyri*), etc.

The agrohorticultural insecticide containing the sulfonamide derivative of general formula (I) or salt thereof of the present invention as an active ingredient has a marked controlling effect on the above-exemplified insect pests injurious to paddy field crops, upland crops, fruit trees, vegetables, other crops, flowers and ornamental plants, and the like. Therefore, the desired effect of the agrohorticultural insecticide of the present invention can be obtained by applying the agrohorticultural insecticide to the seeds, paddy field water, stalks and leaves of fruit trees, vegetables, other crops, flowers and ornamental plants, soil, etc., at a season at which the insect pests are expected to appear, before their appearance or at the time when their appearance is confirmed.

The agrohorticultural insecticide of the present invention is generally prepared into conveniently usable forms according to an ordinary manner for preparation of agrochemicals.

That is, the sulfonamide derivative of general formula (I) or a salt thereof and, optionally, an adjuvant are blended with a suitable inert carrier in a proper proportion and prepared into a suitable preparation form such as a suspension, emulsifiable concentrate, soluble concentrate, wettable powder, granules, dust, tablets, pack or the like through dissolution, dispersion, suspension, mixing, impregnation, adsorption or sticking.

The inert carrier usable in the present invention may be either solid or liquid. As a material usable as the solid carrier, there can be exemplified soybean flour, cereal flour, wood flour, bark flour, saw dust, powdered tobacco stalks, powdered walnut shells, bran, powdered cellulose, extraction residues of vegetables, powdered synthetic polymers or resins, clay (e.g. kaolin, bentonite, and acid clay), talcs (e.g. talc and pyrophyllite), silica powders or flakes {e.g. diatomaceous earth, silica sand, mica and white carbon (synthetic, high-dispersion silicic acid, also called finely divided hydrated silica or hydrated silicic acid, some of commercially available products contain calcium silicate as the major component)}, activated carbon, powdered sulfur, pumice, calcined diatomaceous earth, ground brick, fly ash, sand, calcium carbonate, calcium phosphate and other inorganic or mineral powders, plastic carriers (e.g. polyethylenes, polypropylenes and poly(vinylidene chloride)s), chemical fertilizers (e.g. ammonium sulfate, ammonium phosphate, ammonium nitrate, urea and ammonium chloride), and compost. These materials may be used alone or as a mixture of two or more thereof.

A material usable as the liquid carrier is selected from materials that have solubility in themselves or which are without such solubility but are capable of dispersing a compound as active ingredient with the aid of an adjuvant. The following are typical examples of the liquid carrier and can be used alone or as a mixture of two or more thereof: water; alcohols (e.g. methanol, ethanol, isopropanol, butanol and ethylene glycol), ketones (e.g. acetone, methyl ethyl ketone, methyl isobutyl ketone, diisobutyl ketone and cyclohexanone), ethers (e.g. ethyl ether, dioxane, Cellosolve, dipropyl ether and tetrahydrofuran), aliphatic hydrocarbons (e.g. kerosene and mineral oils), aromatic hydrocarbons (e.g. benzene, toluene, xylene, solvent naphtha and alkylnaphthalenes), halogenated hydrocarbons (e.g. dichloroethane, chloroform, carbon tetrachloride and chlorobenzene), esters (e.g. ethyl acetate, diisopropyl phthalate, dibutyl phthalate and dioctyl phthalate), amides (e.g. dimethylformamide, diethylformamide and dimethylacetamide), nitriles (e.g. acetonitrile), and dimethyl sulfoxide.

The following are typical examples of the adjuvant, which are used depending upon purposes and used alone or in combination in some cases, or need not be used at all.

To emulsify, disperse, dissolve and/or wet a compound as active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

Further, to stabilize the dispersion of a compound as active ingredient, tackify it and/or bind it, the adjuvants exemplified below may also be used, namely, there may also be used adjuvants such as casein, gelatin, starch, methyl cellulose, carboxymethyl cellulose, gum arabic, poly(vinyl alcohol)s, turpentine, bran oil, bentonite and ligninsulfonates.

To improve the flowability of a solid product, the following adjuvants may also be used, namely, there may be used adjuvants such as waxes, stearates, alkyl phosphates, etc.

Adjuvants such as naphthalenesulfonic acid condensation products and polycondensates of phosphates may be used as a peptizer for dispersible products.

Adjuvants such as silicone oil may also be used as a defoaming agent.

Further, if necessary, functional spreading agents, active enhancers such as metabolic decomposition inhibitor like piperonyl butoxide, antifreezing agents such as propylene glycol, antioxidants such as BHT, ultraviolet absorbers, and the like may also be added.

The content of the compound as active ingredient may be varied as required, and may be properly chosen in the range of 0.01 to 90 parts by weight per 100 parts by weight of the agrohorticultural insecticide. For example, in dusts or granules, the suitable content of the compound as active ingredient is from 0.01 to 50 parts by weight. In emulsifiable concentrates or flowable wettable powders, it is also from 0.01 to 50 parts by weight.

The agrohorticultural insecticide of the present invention is used to control a variety of insect pests in the following manner: it is applied to a crop on which the insect pests are expected to appear, or a site where appearance or growth of the insect pests is undesirable, as it is or after being properly diluted with or suspended in water or the like, in an amount effective for control of the insect pests.

The applying dosage of the agrohorticultural insecticide of the present invention is varied depending upon various factors such as a purpose, insect pests to be controlled, a growth stage of a plant, tendency of insect pests appearance, weather, environmental conditions, a preparation form, an application method, an application site and application time. It may be properly chosen in the range of 0.001 g to 10 kg, preferably 0.01 g to 1 kg, (in terms of the compound as active ingredient) per 10 areas depending upon purposes.

The agrohorticultural insecticide of the present invention may be used in admixture with other agrohorticultural insecticides, acaricides, nematocides, fungicides, biotic pesticides or the like in order to expand both spectrum of controllable insect pest species and the period of time when effective application is possible or to reduce the dosage. Furthermore, the agrohorticultural insecticide of the present invention may be used in admixture with herbicides, plant growth regulators, fertilizers or the like, depending upon application situations.

Typical formulation examples and test examples of the present invention are described below but they should not be construed as limiting the scope of the invention.

As used in the formulation examples, the terms "part" and "parts" are by weight.

Formulation Example 1

| | |
|---|---|
| Each compound listed in Table 1 or 2 | 10 parts |
| Xylene | 70 parts |
| N-methylpyrrolidone | 10 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

Formulation Example 2

| | |
|---|---|
| Each compound listed in Table 1 or 2 | 3 parts |
| Clay powder | 82 parts |
| Diatomaceous earth powder | 15 parts |

A dust was prepared by mixing uniformly and grinding the above ingredients.

Formulation Example 3

| | |
|---|---|
| Each compound listed in Table 1 or 2 | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

Formulation Example 4

| Each compound listed in Table 1 or 2 | 20 parts |
|---|---|
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1

Insecticidal Effect on Diamond Back Moth
(*Plutella xylostella*)

Adult diamond back moths were released and allowed to oviposit on a Chinese cabbage seedling. Two days after the release, the seedling having the eggs deposited thereon was immersed for about 30 seconds in a liquid chemical prepared by diluting a preparation containing each compound listed in Table 1 or 2 as an active ingredient to adjust the concentration to 50 ppm. After air-dryness, it was allowed to stand in a room thermostated at 25° C.

Six days after the immersion, the hatched insects were counted. The mortality was calculated according to the following equation and the insecticidal effect was judged according to the criterion shown below. The test was carried out with triplicate groups of 10 insects.

$$\text{Corrected mortality } (\%) = \frac{\text{Number of hatched insects in untreated group} - \text{Number of hatched insects in treated group}}{\text{Number of hatched insects in untreated group}} \times 100$$

Criterion for Judgment:
A - - - Mortality 100%
B - - - Mortality 99–90%
C - - - Mortality 89–80%
D - - - Mortality 79–50%
E - - - Mortality less than 50%

The result of the above test is shown in Table 4 below.

Test Example 2

Insecticidal Effect on Common Cutworm
(*Spodoptera litura*)

A piece of cabbage leaf (cultivar: Shikidori) was immersed for about 30 seconds in a liquid chemical prepared by diluting a preparation containing each compound listed in Table 1 or 2 as an active ingredient to adjust the concentration to 50 ppm. After air-dryness, it was placed in a plastic Petri dish with a diameter of 9 cm and inoculated with second-instar larvae of common cutworm, after which the dish was closed and then allowed to stand in a room thermostated at 25° C. Eight days after the inoculation, the dead and alive were counted. The mortality was calculated according to the following equation and the insecticidal effect was judged according to the criterion shown in Test Example 1. The test was carried out with triplicate groups of 10 insects.

$$\text{Corrected mortality } (\%) = \frac{\text{Number of alive larvae in untreated group} - \text{Number of alive larvae in treated group}}{\text{Number of alive larvae in untreated group}} \times 100$$

The result of the above test is shown in Table 4 below.

Test Example 3

Insecticidal Effect on Smaller Tea Tortrix
(*Adoxophyes sp.*)

Tea leaves were immersed for about 30 seconds in a liquid chemical prepared by diluting a preparation containing each compound listed in Table 1 or 2 as an active ingredient to adjust the concentration to 50 ppm. After air-dryness, the tea leaves were placed in a plastic Petri dish with a diameter of 9 cm and inoculated with larvae of smaller tea tortrix, after which the dish was allowed to stand in a room thermostated at 25° C. and having a humidity of 70%. Eight days after the inoculation, the dead and alive were counted and the insecticidal effect was judged according to the criterion shown in Test Example 1. The test was carried out with triplicate groups of 10 insects.

The result of the above test is shown in Table 4 below.

TABLE 4

| No | Test Example 1 | Test Example 2 | Test Example 3 |
|---|---|---|---|
| 1-1 | A | A | A |
| 1-2 | A | A | A |
| 1-3 | A | A | A |
| 1-4 | A | A | A |
| 1-6 | A | A | A |
| 1-7 | A | A | A |
| 1-8 | A | A | A |
| 1-12 | A | A | A |
| 1-14 | A | A | A |
| 1-20 | A | A | A |
| 1-21 | A | A | A |
| 1-22 | A | A | A |
| 1-23 | A | A | A |
| 1-24 | A | A | A |
| 1-25 | A | A | A |
| 1-27 | A | A | A |
| 1-28 | A | A | A |
| 1-29 | A | A | A |
| 1-30 | A | A | A |
| 1-31 | A | A | A |
| 1-32 | A | A | A |
| 1-35 | A | A | A |
| 1-36 | A | A | A |
| 1-37 | A | A | A |
| 1-38 | A | A | A |
| 1-39 | A | A | A |
| 1-40 | A | A | A |
| 1-41 | A | A | A |
| 1-42 | A | A | A |
| 1-43 | A | A | A |
| 1-44 | A | A | A |
| 1-45 | A | A | A |
| 1-46 | A | A | A |

TABLE 4-continued

| No | Test Example 1 | Test Example 2 | Test Example 3 |
|---|---|---|---|
| 1-47 | A | A | A |
| 1-48 | A | C | A |
| 1-54 | A | A | A |
| 1-55 | A | A | A |
| 1-56 | A | A | A |
| 1-57 | A | A | A |
| 1-58 | A | A | E |
| 1-59 | A | A | E |
| 1-60 | A | A | E |
| 1-61 | A | A | A |
| 1-62 | A | A | A |
| 1-63 | A | A | A |
| 1-66 | A | A | A |
| 1-67 | A | E | E |
| 1-71 | A | A | A |
| 1-72 | A | A | A |
| 1-73 | A | A | A |
| 1-75 | A | A | A |
| 1-76 | A | A | A |
| 1-77 | A | A | A |
| 1-78 | A | E | A |
| 1-79 | A | A | A |
| 1-80 | A | A | A |
| 1-81 | A | A | A |
| 1-82 | A | A | A |
| 1-83 | A | A | A |
| 1-84 | A | A | A |
| 1-85 | A | A | A |
| 1-86 | A | A | A |
| 1-87 | A | A | A |
| 1-88 | A | A | A |
| 1-89 | A | A | A |
| 1-91 | A | A | A |
| 1-92 | A | A | A |
| 1-93 | A | A | A |
| 1-94 | A | A | A |
| 1-103 | A | A | A |
| 1-104 | A | A | A |
| 1-105 | A | A | E |
| 1-106 | A | E | E |
| 1-107 | A | C | A |
| 1-108 | A | A | A |
| 1-109 | A | E | A |
| 1-110 | A | E | E |
| 1-111 | A | E | E |
| 1-112 | A | E | E |
| 1-116 | A | D | A |
| 1-121 | A | E | E |
| 1-142 | A | A | A |
| 1-144 | A | A | A |
| 1-146 | A | A | A |
| 1-147 | A | A | A |
| 1-148 | A | A | A |
| 1-149 | A | A | A |
| 1-175 | A | A | A |
| 1-176 | A | A | A |
| 1-177 | A | A | A |
| 1-178 | A | A | A |
| 1-179 | A | A | A |
| 1-180 | A | C | A |
| 1-181 | A | A | A |
| 1-184 | A | A | A |
| 1-200 | A | A | A |
| 1-201 | A | A | A |
| 1-207 | A | A | E |
| 1-208 | A | E | A |
| 1-211 | A | A | A |
| 1-212 | A | A | A |
| 1-213 | A | A | A |
| 1-214 | A | A | A |
| 1-215 | A | A | A |
| 1-216 | A | A | A |
| 1-217 | A | A | A |
| 1-218 | A | A | A |
| 1-219 | A | A | A |
| 1-266 | A | C | E |
| 1-267 | A | C | E |
| 1-268 | A | A | A |
| 1-275 | A | E | E |
| 1-276 | A | E | E |
| 1-277 | A | A | A |
| 1-285 | A | C | E |
| 1-286 | A | A | E |
| 1-301 | A | A | A |
| 1-302 | A | A | A |
| 1-303 | A | A | A |
| 1-304 | A | A | A |
| 1-305 | A | A | A |
| 1-306 | A | A | A |
| 1-307 | A | A | A |
| 1-308 | A | A | A |
| 1-309 | A | A | A |
| 1-310 | A | A | A |
| 1-342 | A | A | A |
| 1-343 | A | A | A |
| 1-344 | A | A | A |
| 1-345 | A | A | A |
| 2-5 | A | A | A |
| 2-7 | A | A | A |
| 2-16 | A | E | A |

The invention claimed is:

1. A sulfonamide derivative represented by general formula (I) or a salt thereof:

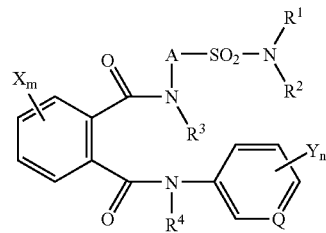

wherein A is a $(C_1–C_6)$alkylene group;

$R^1$ is a hydrogen atom; a $(C_1–C_6)$ alkyl group; a substituted $(C_1–C_6)$alkyl group having one or more substituents which may be the same or different and are selected from halogen atoms, hydroxyl group, $(C_1–C_6)$ alkoxy groups, $(C_1–C_6)$ alkylthio groups, $(C_1–C_6)$ alkylsulfinyl groups, $(C_1–C_6)$ alkylsulfonyl groups, $(C_1–C_6)$ alkylaminocarbonyl groups, $(C_1–C_6)$ alkylcarbonyloxy groups, phenylthio group, phenyl group, substituted phenyl groups having one or more substituents which may be the same or different and are selected from halogen atoms, cyano group, nitro group, $(C_1–C_6)$ alkyl groups, $(C_1–C_6)$ alkoxy groups, halo $(C_1–C_6)$ alkylthio groups, and pyridyl group; a $(C_3–C_6)$ alkenyl group; a $(C_3–C_6)$ alkynyl group; a $(C_3–C_6)$cycloalkyl group; a hydroxyl group; a $(C_1–C_6)$alkoxy group; an amino group, a phenylamino group, a substituted phenylamino group having on the ring one or more substituents which may be the same or different and are selected from halogen atoms, $(C_1–C_6)$alkoxy groups and $(C_1–C_6)$alkylthio groups; or a pyridyl group;

each of $R^2$, $R^3$ and $R^4$, which may be the same or different, is a hydrogen atom, a $(C_1–C_6)$alkyl group, a $(C_3–C_6)$ alkenyl group, a $(C_3–C_6)$ alkynyl group, a $(C_1–C_4)$ alkoxy$(C_1–C_4)$alkyl group or a $(C_1–C_4)$ alkylthio $(C_1–C_4)$alkyl group, $R^2$ being able to bind to A or $R^1$ to form a 3- to 8-membered ring which may contain one to three atoms that may be the same or different and are selected from oxygen atom, sulfur atom and nitrogen atom, and which ring may have one or more substituents that may be the same or different and are selected from halogen atoms, $(C_1-C_6)$ alkyl groups and $(C_1-C_6)$ alkoxy groups;

Q is a carbon atom or a nitrogen atom;

each of Xs, which may be the same or different, is a halogen atom, a nitro group, a $(C_1-C_6)$alkyl group, a halo $(C_1-C_6)$ alkyl group, a $(C_2-C_6)$ alkenyl group, a halo $(C_2-C_6)$ alkenyl group, a $(C_2-C_6)$ alkynyl group halo $(C_3-C_6)$ alkynyl group, a $(C_1-C_6)$alkoxy group, a halo $(C_1-C_6)$ alkoxy group, a $(C_1-C_6)$alkylcarbonyloxy group, a halo$(C_1-C_6)$alkylcarbonyloxy group, a $(C_1-C_6)$ alkylthio group, a halo $(C_1-C_6)$ alkylthio group, a $(C_1-C_6)$ aikylsulfinyl group, a halo $(C_1-C_6)$ alkylsulfinyl group, a $(C_1-C_6)$ alkylsulfonyl group, a halo$(C_1-C_6)$alkylsulfonyl group, a $(C_1-C_6)$alkylsulfonyloxy group or a haio$(C_1-C_6)$alkylsulfonyloxy group, m is an integer of 0 to 1:

each of Ys, which may be the same or different, is a halogen atom; a $(C_1-C_6)$alkyl group; a halo $(C_1-C_6)$ alkyl group; or a halo $(C_1-C_6)$ alkoxy group; and n is an integer of 1 to 3.

2. An agricultural and horticultural insecticide characterized by containing a sulfonamide derivative of general formula (I) or a salt thereof according to claim 1 as an active ingredient.

3. A method for applying an agricultural and horticultural insecticide, characterized by treating a crop plant to be protected, soil or a paddy field with an effective amount of an agricultural and horticultural insecticide according to claim 2 in order to protect useful plants against insect pests.

* * * * *